(12) United States Patent
Warburton

(10) Patent No.: US 8,100,910 B2
(45) Date of Patent: Jan. 24, 2012

(54) INTRAMEDULLARY INTERLOCKING FIXATION DEVICES FOR THE DISTAL RADIUS

(75) Inventor: Mark J. Warburton, High Point, NC (US)

(73) Assignee: Piper Medical, Inc., High Point, NC (US)

( * ) Notice: Subject to any disclaimer, the term of this patent is extended or adjusted under 35 U.S.C. 154(b) by 3 days.

(21) Appl. No.: 12/391,459

(22) Filed: Feb. 24, 2009

(65) Prior Publication Data

US 2009/0157080 A1 Jun. 18, 2009

Related U.S. Application Data

(63) Continuation of application No. 11/381,231, filed on May 2, 2006, now Pat. No. 7,713,271, which is a continuation of application No. 10/377,255, filed on Feb. 28, 2003, now Pat. No. 7,160,302, which is a continuation of application No. 09/668,941, filed on Sep. 22, 2000, now Pat. No. 6,527,775.

(51) Int. Cl.
*A61B 17/58* (2006.01)
*A61F 2/30* (2006.01)
(52) U.S. Cl. .......................................... 606/64
(58) Field of Classification Search .................. 606/53, 606/60, 62–68
See application file for complete search history.

(56) References Cited

U.S. PATENT DOCUMENTS

| | | | |
|---|---|---|---|
| 2,500,370 A | 3/1950 | McKibbin | |
| 2,682,265 A | 6/1954 | Collison | |
| 3,334,624 A | 8/1967 | Schneider et al. | |
| 3,433,220 A | 3/1969 | Zickel | |
| 3,709,218 A | 1/1973 | Halloran | |
| 3,741,205 A | 6/1973 | Markolf et al. | |
| 3,760,802 A | 9/1973 | Fischer et al. | |
| 3,781,917 A | 1/1974 | Mathys | |
| 3,939,498 A | 2/1976 | Lee et al. | |
| 3,973,278 A | 8/1976 | Shersher | |
| 3,977,398 A | 8/1976 | Burstein | |
| 4,011,863 A | 3/1977 | Zickel | |
| 4,055,172 A | 10/1977 | Ender et al. | |
| 4,091,806 A | 5/1978 | Aginsky | |
| 4,101,985 A | 7/1978 | Baumann et al. | |
| 4,103,683 A | 8/1978 | Neufeld | |
| 4,135,507 A | 1/1979 | Harris | |
| 4,169,470 A | 10/1979 | Ender et al. | |
| 4,227,518 A | 10/1980 | Aginsky | |
| 4,237,875 A | 12/1980 | Termanini | |

(Continued)

FOREIGN PATENT DOCUMENTS

DE 7115713 6/1975

(Continued)

OTHER PUBLICATIONS

Abstract, XP-002193640 (Jan. 7, 1993).

(Continued)

*Primary Examiner* — Anu Ramana
(74) *Attorney, Agent, or Firm* — Myers Bigel Sibley & Sajovec, P.A.

(57) ABSTRACT

Methods and devices for treating fractures in or adjacent the wrist and distal forearm employ an intramedullary interlocking fixation rod (i.e, it interlocks the distal and proximal fracture fragments together) to stabilize the skeletal structure in a manner which can inhibit the amount of collapse or loss in skeletal length exhibited by a patient with a distal radius fracture.

26 Claims, 21 Drawing Sheets

U.S. PATENT DOCUMENTS

| | | |
|---|---|---|
| 4,338,926 A | 7/1982 | Kummer et al. |
| 4,393,868 A | 7/1983 | Teague |
| 4,423,721 A | 1/1984 | Otte et al. |
| 4,446,857 A | 5/1984 | Otte et al. |
| 4,453,539 A | 6/1984 | Raftopoulos et al. |
| 4,467,793 A | 8/1984 | Ender |
| 4,473,069 A | 9/1984 | Kolmert |
| 4,475,545 A | 10/1984 | Ender |
| 4,483,335 A | 11/1984 | Tornier |
| 4,493,317 A | 1/1985 | Klaue |
| 4,503,847 A | 3/1985 | Mouradian |
| 4,513,744 A | 4/1985 | Klaue |
| 4,522,202 A | 6/1985 | Otte et al. |
| 4,541,424 A | 9/1985 | Grosse et al. |
| 4,590,930 A | 5/1986 | Kurth et al. |
| 4,622,959 A * | 11/1986 | Marcus ................ 606/64 |
| 4,630,601 A | 12/1986 | Harder et al. |
| 4,653,487 A * | 3/1987 | Maale ................ 606/62 |
| 4,667,663 A | 5/1987 | Miyata |
| 4,697,585 A | 10/1987 | Williams |
| 4,705,027 A | 11/1987 | Klaue |
| 4,712,541 A | 12/1987 | Harder et al. |
| 4,733,654 A | 3/1988 | Marino |
| 4,775,381 A | 10/1988 | Tari et al. |
| 4,776,330 A | 10/1988 | Chapman et al. |
| 4,781,181 A | 11/1988 | Tanguy |
| 4,794,919 A | 1/1989 | Nilsson |
| 4,805,607 A | 2/1989 | Engelhardt et al. |
| 4,846,162 A | 7/1989 | Moehring |
| 4,854,312 A | 8/1989 | Raftopoulos et al. |
| 4,858,602 A | 8/1989 | Seidel et al. |
| 4,875,474 A | 10/1989 | Border |
| 4,875,475 A | 10/1989 | Comte et al. |
| 4,877,019 A | 10/1989 | Vives |
| 4,881,535 A | 11/1989 | Sohngen |
| 4,911,153 A | 3/1990 | Border |
| 4,943,291 A | 7/1990 | Tanguy |
| 4,944,764 A | 7/1990 | Stossel |
| 4,946,549 A | 8/1990 | Bachman et al. |
| 4,976,258 A | 12/1990 | Richter et al. |
| 4,976,714 A | 12/1990 | Aghion |
| 4,998,912 A | 3/1991 | Scarbrough et al. |
| 5,013,314 A | 5/1991 | Firica et al. |
| 5,035,697 A | 7/1991 | Frigg |
| 5,041,115 A | 8/1991 | Frigg et al. |
| 5,057,103 A | 10/1991 | Davis |
| 5,057,110 A | 10/1991 | Kranz et al. |
| 5,066,296 A | 11/1991 | Chapman et al. |
| 5,084,053 A | 1/1992 | Ender |
| 5,100,404 A | 3/1992 | Hayes |
| 5,122,141 A | 6/1992 | Simpson et al. |
| 5,122,146 A | 6/1992 | Chapman et al. |
| 5,135,527 A | 8/1992 | Ender |
| 5,167,666 A | 12/1992 | Mattheck et al. |
| 5,190,543 A | 3/1993 | Schlapfer |
| 5,197,966 A | 3/1993 | Sommerkamp |
| 5,201,735 A | 4/1993 | Chapman et al. |
| 5,211,645 A | 5/1993 | Baumgart et al. |
| 5,239,569 A | 8/1993 | Saleh et al. |
| 5,248,313 A | 9/1993 | Greene et al. |
| 5,263,955 A | 11/1993 | Baumgart et al. |
| 5,268,000 A | 12/1993 | Ottieri et al. |
| 5,281,224 A | 1/1994 | Faccioli et al. |
| 5,295,991 A | 3/1994 | Frigg |
| 5,300,074 A | 4/1994 | Frigg |
| 5,334,192 A | 8/1994 | Behrens |
| 5,352,228 A | 10/1994 | Kummer et al. |
| 5,356,410 A | 10/1994 | Pennig |
| 5,364,399 A | 11/1994 | Lowery et al. |
| 5,375,956 A | 12/1994 | Pennig |
| 5,397,328 A | 3/1995 | Behrens et al. |
| 5,411,503 A | 5/1995 | Hollstien et al. |
| 5,415,660 A | 5/1995 | Campbell et al. |
| 5,429,638 A | 7/1995 | Muschler et al. |
| 5,433,718 A | 7/1995 | Brinker |
| 5,441,500 A | 8/1995 | Seidel et al. |
| 5,443,466 A | 8/1995 | Shah |
| 5,458,654 A | 10/1995 | Tepic |
| 5,472,444 A | 12/1995 | Huebner et al. |
| 5,484,438 A | 1/1996 | Pennig |
| 5,499,986 A | 3/1996 | Dimarco |
| 5,536,269 A | 7/1996 | Spievack |
| 5,549,610 A | 8/1996 | Russell et al. |
| 5,569,249 A * | 10/1996 | James et al. ................ 606/62 |
| 5,569,262 A | 10/1996 | Carney |
| 5,571,103 A | 11/1996 | Bailey |
| 5,573,536 A | 11/1996 | Grosse et al. |
| 5,578,035 A | 11/1996 | Lin |
| 5,586,985 A | 12/1996 | Putnam et al. |
| 5,618,286 A | 4/1997 | Brinker |
| 5,620,445 A | 4/1997 | Brosnahan et al. |
| 5,620,449 A | 4/1997 | Faccioli et al. |
| 5,626,579 A | 5/1997 | Muschler et al. |
| 5,643,258 A | 7/1997 | Robioneck et al. |
| 5,645,545 A | 7/1997 | Bryant |
| 5,653,709 A | 8/1997 | Frigg |
| 5,658,283 A | 8/1997 | Huebner |
| 5,658,287 A | 8/1997 | Hofmann et al. |
| 5,665,086 A | 9/1997 | Itoman et al. |
| 5,681,318 A | 10/1997 | Pennig et al. |
| 5,690,634 A | 11/1997 | Muller et al. |
| 5,697,930 A | 12/1997 | Itoman et al. |
| 5,697,934 A | 12/1997 | Huebner |
| 5,713,901 A | 2/1998 | Tock |
| 5,713,902 A | 2/1998 | Friedl |
| 5,718,704 A | 2/1998 | Medoff |
| 5,766,174 A | 6/1998 | Perry |
| 5,766,179 A | 6/1998 | Faccioli et al. |
| 5,766,180 A | 6/1998 | Winquist |
| 5,776,194 A | 7/1998 | Mikol et al. |
| 5,779,705 A | 7/1998 | Matthews |
| 5,800,437 A | 9/1998 | Gustilo et al. |
| 5,853,413 A | 12/1998 | Carter et al. |
| 5,928,235 A | 7/1999 | Friedl |
| 5,941,878 A | 8/1999 | Medoff |
| 5,954,722 A | 9/1999 | Bono |
| 5,961,553 A | 10/1999 | Coty et al. |
| 5,976,134 A | 11/1999 | Huebner |
| 5,997,490 A | 12/1999 | McLeod et al. |
| 6,001,101 A | 12/1999 | Augagneur et al. |
| 6,010,505 A | 1/2000 | Asche et al. |
| 6,010,506 A | 1/2000 | Gosney et al. |
| 6,019,761 A | 2/2000 | Gustilo |
| 6,022,349 A | 2/2000 | McLeod et al. |
| 6,027,506 A | 2/2000 | Faccioli et al. |
| 6,033,407 A | 3/2000 | Behrens |
| 6,056,755 A | 5/2000 | Horas et al. |
| 6,074,392 A | 6/2000 | Durham |
| 6,077,264 A | 6/2000 | Chemello |
| 6,080,159 A | 6/2000 | Vichard |
| 6,093,192 A | 7/2000 | Abel |
| 6,096,040 A | 8/2000 | Esser |
| 6,120,504 A | 9/2000 | Brumback et al. |
| 6,123,708 A | 9/2000 | Kilpela et al. |
| 6,123,709 A | 9/2000 | Jones |
| 6,126,661 A | 10/2000 | Faccioli et al. |
| 6,146,384 A | 11/2000 | Lee et al. |
| 6,200,321 B1 | 3/2001 | Orbay et al. |
| 6,206,880 B1 | 3/2001 | Karladani |
| 6,221,073 B1 | 4/2001 | Weiss et al. |
| 6,221,074 B1 | 4/2001 | Cole et al. |
| 6,224,601 B1 | 5/2001 | Friedl |
| 6,228,086 B1 | 5/2001 | Wahl et al. |
| 6,231,576 B1 | 5/2001 | Frigg et al. |
| 6,245,075 B1 | 6/2001 | Betz et al. |
| 6,248,109 B1 | 6/2001 | Stoffella |
| 6,261,289 B1 | 7/2001 | Levy |
| 6,270,499 B1 | 8/2001 | Leu et al. |
| 6,273,892 B1 | 8/2001 | Orbay et al. |
| 6,283,969 B1 | 9/2001 | Grusin et al. |
| 6,296,645 B1 | 10/2001 | Hover et al. |
| 6,319,253 B1 | 11/2001 | Ackeret et al. |
| 6,355,069 B1 | 3/2002 | DeCarlo et al. |
| 6,358,250 B1 | 3/2002 | Orbay |
| 6,364,882 B1 | 4/2002 | Orbay |
| 6,379,359 B1 | 4/2002 | Dahners |
| 6,379,360 B1 | 4/2002 | Ackeret et al. |

| | | | |
|---|---|---|---|
| 6,383,185 B1 | 5/2002 | Baumgart |
| 6,387,098 B1 | 5/2002 | Cole et al. |
| 6,395,033 B1 | 5/2002 | Pepper |
| 6,402,753 B1 | 6/2002 | Cole et al. |
| 6,409,768 B1 | 6/2002 | Tepic et al. |
| 6,416,516 B1 | 7/2002 | Stauch et al. |
| 6,423,066 B1 | 7/2002 | Harder et al. |
| 6,440,135 B2 | 8/2002 | Orbay et al. |
| 6,443,954 B1 | 9/2002 | Bramlet et al. |
| 6,461,360 B1 | 10/2002 | Adam |
| 6,488,684 B2 | 12/2002 | Sterghos et al. |
| 6,508,819 B1 | 1/2003 | Orbay |
| 6,508,820 B2 | 1/2003 | Bales |
| 6,514,253 B1 | 2/2003 | Yao |
| 6,524,313 B1 | 2/2003 | Fassier et al. |
| 6,524,314 B1 | 2/2003 | Dean et al. |
| 6,527,775 B1 | 3/2003 | Warburton |
| 6,533,788 B1 | 3/2003 | Orbay |
| 6,547,791 B1 | 4/2003 | Buhren et al. |
| 6,554,833 B2 | 4/2003 | Levy et al. |
| 6,572,620 B1 | 6/2003 | Schon et al. |
| 6,579,294 B2 | 6/2003 | Robioneck |
| 6,607,531 B2 | 8/2003 | Frigg |
| 6,629,976 B1 | 10/2003 | Gnos et al. |
| 6,648,889 B2 | 11/2003 | Bramlet et al. |
| 6,652,529 B2 | 11/2003 | Swanson |
| 6,658,189 B2 | 12/2003 | Ajima et al. |
| 6,660,009 B1 | 12/2003 | Azar |
| 6,702,823 B2 | 3/2004 | Iaia |
| 6,706,046 B2 | 3/2004 | Orbay et al. |
| 6,709,436 B1 | 3/2004 | Hover et al. |
| 6,730,087 B1 | 5/2004 | Butsch |
| 6,730,090 B2 | 5/2004 | Orbay et al. |
| 6,736,818 B2 | 5/2004 | Perren et al. |
| 6,755,862 B2 | 6/2004 | Keynan |
| 6,767,351 B2 | 7/2004 | Orbay et al. |
| 6,786,908 B2 | 9/2004 | Hover et al. |
| 6,793,659 B2 | 9/2004 | Putnam |
| 6,796,984 B2 | 9/2004 | Soubeiran |
| 6,808,527 B2 | 10/2004 | Lower et al. |
| 6,866,665 B2 | 3/2005 | Orbay |
| 6,893,444 B2 | 5/2005 | Orbay |
| 6,926,720 B2 | 8/2005 | Castaneda |
| 7,008,425 B2 | 3/2006 | Phillips |
| 7,018,380 B2 | 3/2006 | Cole |
| 7,033,365 B2 | 4/2006 | Powell et al. |
| 7,041,104 B1 | 5/2006 | Cole et al. |
| 7,066,943 B2 | 6/2006 | Zirkle, Jr. |
| 7,247,156 B2 | 7/2007 | Ekholm et al. |
| 2001/0011172 A1 | 8/2001 | Orbay et al. |
| 2002/0032446 A1 | 3/2002 | Orbay |
| 2002/0143337 A1 | 10/2002 | Orbay et al. |
| 2002/0143338 A1 | 10/2002 | Orbay et al. |
| 2002/0156474 A1 | 10/2002 | Wack et al. |
| 2002/0183753 A1 | 12/2002 | Manderson |
| 2003/0055428 A1 | 3/2003 | Swanson |
| 2003/0069581 A1 | 4/2003 | Stinson et al. |
| 2003/0073999 A1 | 4/2003 | Putnam |
| 2003/0083660 A1 | 5/2003 | Orbay |
| 2003/0083661 A1 | 5/2003 | Orbay et al. |
| 2003/0105461 A1 | 6/2003 | Putnam |
| 2006/0015101 A1 | 1/2006 | Warburton et al. |
| 2006/0015123 A1 | 1/2006 | Fencl et al. |

FOREIGN PATENT DOCUMENTS

| | | |
|---|---|---|
| EP | 0091499 | 10/1983 |
| EP | 0118778 | 3/1987 |
| EP | 0 649 289 B1 | 5/1992 |
| EP | 0547380 A1 | 6/1993 |
| EP | 1 095 626 A1 | 5/2001 |
| EP | 1330988 | 7/2003 |
| FR | 2586554 | 8/1985 |
| FR | 2668360 | 10/1990 |
| GB | 1428653 UK | 3/1976 |
| WO | WO 98/18397 | 5/1998 |
| WO | WO 01/56452 A2 | 1/2001 |
| WO | WO 01/56452 A3 | 8/2001 |
| WO | WO 03/037160 A2 | 10/2002 |
| WO | WO 03/037160 A3 | 5/2003 |

OTHER PUBLICATIONS

Canale, S. Terry, Campbell's Operative Orthopaedics, © 1998, Ninth Edition, vol. 3;Chapter 49, pp. 2336-2357 • p. 2345 citing True-Flex prebent titanium nonreamed forearm nails. Nails available from Encore Orthopedics, Austin, TX ( www.encoremed.com) • p. 2346 citing SST forearm intramedullary nail for ulna and radius forearm shaft fractures from Biomet Inc. located in Warsaw, IN ( www.Biomet.com) • p. 2346 Fig. 49-99 citing ForeSight nail system for ulna and radius shaft fractures from Smith & Nephew of Memphis TN ( www.smith-nephew.com).

Damron, T. A. et al., *Biomechanical Analysis of Dorsal Plate Fixation in Proximal Phalangeal Fractures*, Annals of Plastic Surgery, Apr. 2, 1993, pp. 270-275, Little, Brown & Company.

Drobetz, H. et al., *Osteosynthesis of distal radial fractures with a volar locking screw plate system*, International Orthopaedics, Aug. 21, 2002, pp. 1-6, Springer-Verlag 2002.

Fitoussi, F. et al., *Treatment of displaced Intra-Articular Fractures of the Distal End of the Radius with Plates Article*, JBJA Journal of Bone and Joint Surgery-American 1996-1998, Sep. 1997m 17 pages, vol. 27-A, No. 9.

Melone, Charles P., *Distal Radius Fractures: Patterns of Articular Fragmentation*, Orthopedic Clinics of North America, Apr. 1993, pp. 239-253, vol, 24, No. 2.

Orbay, J. et al., *The Treatment of Unstable Distal radius Fractures with Volar Fixation*, Hand Surgery, Dec. 2000, pp. 103-112, vol. 5, No. 2, World Scientific Publishing Company.

Orbay, J. et al., *Voter Fixation for Dorsally Displaced Fractures of the Distal Radius: A Preliminary Report*, The Journal of Hand Surgery, 2002, pp. 205-215, Miami, Florida.

Smith, R. et al., *Open Reduction and Internal Fixation of Volar Lip Fractures of the Distal Radius*, Journal of Orthopaedic Trauma, 1988, pp. 181-187, vol. 2, No. 3, Raven Press, Ltd., New York.

*Smith's Type 1 Fracture*, Fractures of the Hand & Wrist, p. 254.

"Vector Intertrochanteric" BIOMET Medical Products, Inc.( © 1993), 6 pages.

"URTN Unreamed-Tibial Nail" SYNTHES and the AO/ASIF, (date unknown, but thought to be before Sep. 2000 for the purposes of examination), 32 pages.

"The Alta Tibial/Humeral Rod Module for Reamed and Non-Reamed Procedures," Alta Modular Trauma System, Howmedica(1992), 10 pages.

"Proximal Humeral Nailing System: Operative Technique," Stryker Corporation (© 2003), 20 pages.

"MDN Intramedullary Fixation: Metaphyseal/Diaphyseal Solutions," Zimmer, 6 pages (© 2000).

"Uniflex Humeral Nail System," Biomet Inc. (© 1991), 16 pages.

"RAL Nail System: Titanium for Your Most Demanding Cases," ACUMED 00674, 13 pages (date unknown, but thought to be before Sep. 2000 for the purposes of examination).

* cited by examiner

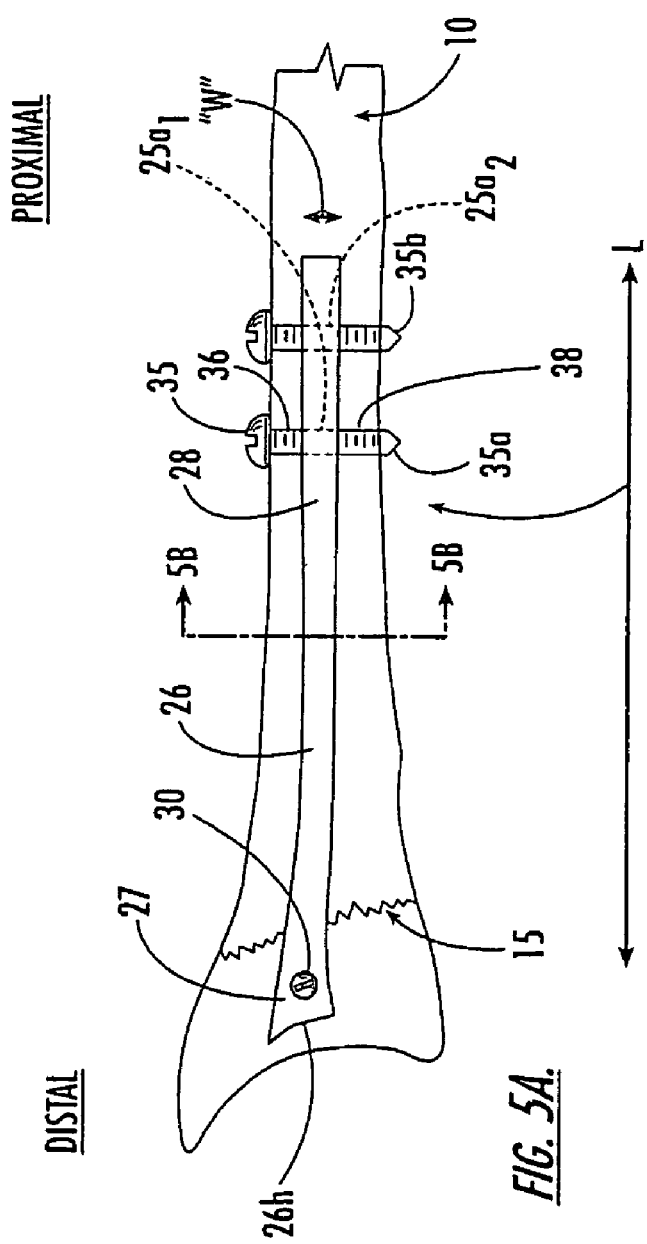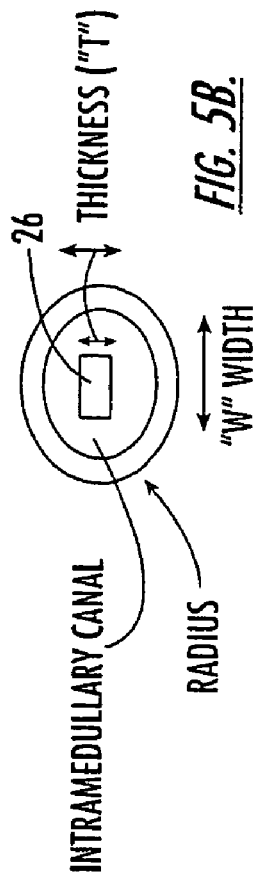

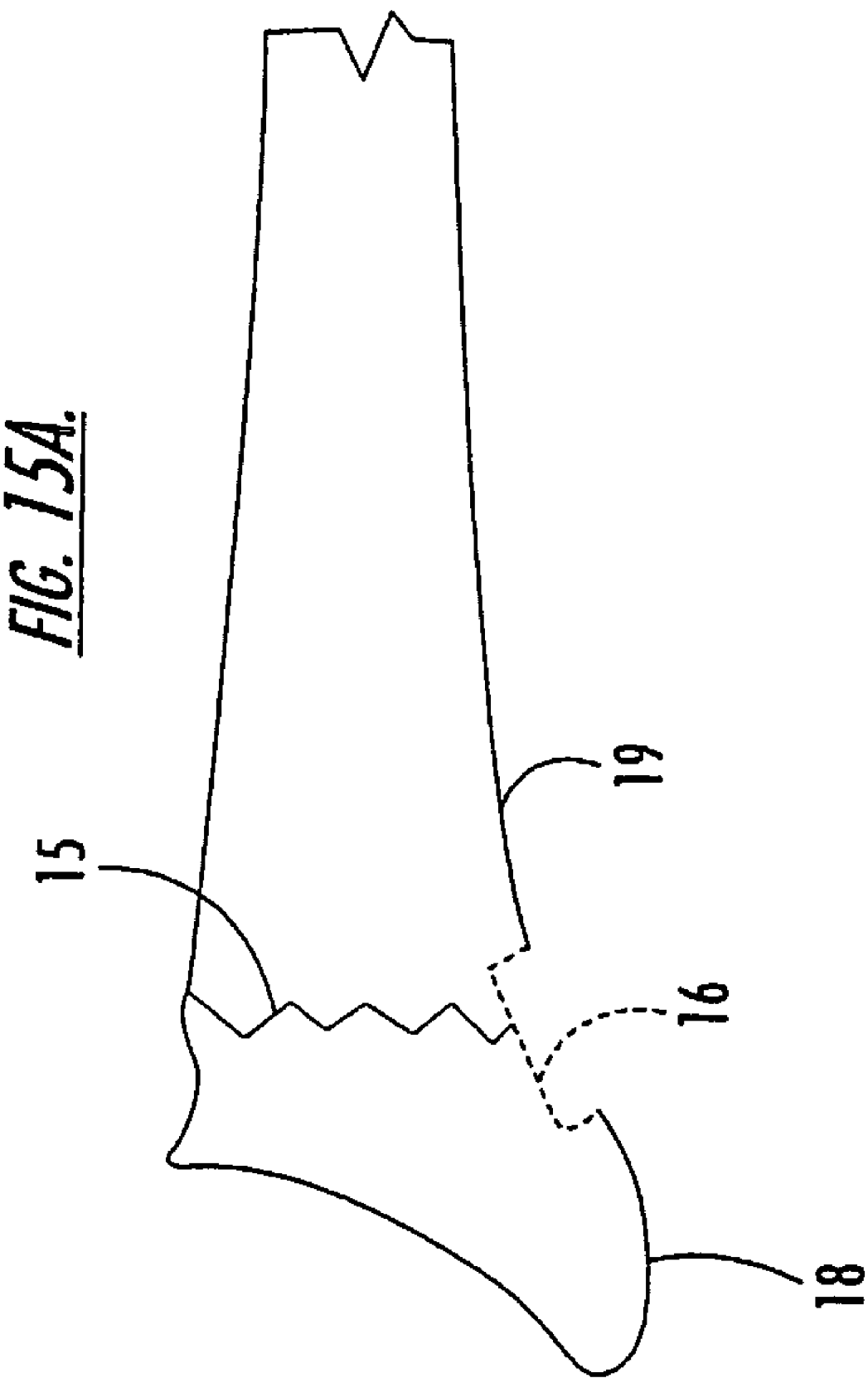

INTRAMEDULLARY INTERLOCKING FIXATION DEVICES FOR THE DISTAL RADIUS

RELATED APPLICATIONS

This application is a continuation of U.S. patent application Ser. No. 11/381,231, filed May 2, 2006, now U.S. Pat. No. 7,713,271, which is a continuation of U.S. patent application Ser. No. 10/377,255, filed Feb. 28, 2003, which issued as U.S. Pat. No. 7,160,302 on Jan. 9, 2007, which is a continuation of application Ser. No. 09/668,941, now U.S. Pat. No. 6,527,775, filed Sep. 22, 2000, and issued Mar. 4, 2003, the contents of which are hereby incorporated by reference as if recited in full herein.

FIELD OF THE INVENTION

This invention relates to devices and methods for treating distal radius fractures.

BACKGROUND OF THE INVENTION

Distal radius fractures are among the most common type of bone fracture of the upper extremities. The distal radius fracture is often called a "Colles" fracture (named after a 19$^{th}$ Century British surgeon who described the fracture). The Colles fracture is associated with a fracture of a distal tip or distal end portion of the radius.

Distal radius fractures are, unfortunately, most common in the elderly segment of the population. This is because the elderly tend to exhibit some degree of bone density loss or osteoporotic condition making their bones more susceptible to injury. Indeed, just as osteoporosis is known to affect women more often and more severely than men, distal radius fractures are much more common in females than males, typically on the order of about 20:1. Distal radius fractures generally occur as a result of a fall, because the patient tends to brace for the fall by outstretching the hand which then fractures upon impact, at the distal radius at or adjacent the wrist.

As shown in FIGS. 1 and 2, the distal radius fracture is such that the major fracture line 15 associated with this type of injury generally occurs just above or proximal to the articular joint surface 11 of the distal radius at the wrist about the metaphysis 12. As shown in FIGS. 1 and 2, one common distal radius fracture type separates the shaft 13 of the radius 10 from the distal end portion of the bone. That is, the fracture line 15 defines a first major bone fragment 18 which is located above the fracture line 15 (the distal side) proximate the articular joint surface 11 and extends substantially medially (laterally) across the radius 10 in the metaphysis region. Although not shown, the fracture may also produce smaller bone fragments or splinters along the fracture line. Further, the distal end portion of the radius may be present as multiple (vertically and/or horizontally oriented) fragments disrupting the articular joint surface itself. This latter type of Colles fracture is known as a comminuted intraarticular fracture (not shown).

FIG. 1 illustrates the fracture line 15 in the radius 10 as a substantially horizontal line which produces an upper or distal fracture fragment 18 as a substantially unitary fragment. Similarly, FIG. 2 illustrates a fracture line 15 in the radius 10 which is offset from a horizontal axis.

Distal radius fractures can be difficult to treat, particularly in the older osteoporotic patient. Conventionally, this type of fracture has been treated by a closed (non-surgical) reduction and application of a splint (such as a plaster compression dressing) or a cast (typically circular plaster or fiberglass). Unfortunately, primarily because of the patient's osteoporosis, during the healing process, and despite the splint/cast immobilization, the fracture fragments can settle, potentially causing a collapse at the fracture line in the distal radius. FIG. 2 illustrates a loss of radial inclination (in degrees) and a shortened length in the skeletal length line (shown with respect to a neutral length line "L") which can occur after a fracture in the distal radius. That is, even healed, these types of fractures may cause shortening or collapse of the bone structure relative to the original skeletal length line. This, in turn, can result in deformity and pain.

Treatment options for a collapsed distal radius fracture are relatively limited. The primary conventional treatments include the use of devices which can be characterized as either external fixation devices or internal fixation devices. External fixation devices are those that stabilize a fracture through the use of percutaneous pins which typically affix one or more bone portions to an external (anchoring or stabilizing) device. Internal fixation devices are those devices which are configured to reside entirely within the subject (internal to the body). Percutaneous pins can be used alone, without anchoring devices, for fixation of Colles type fractures. The use of external devices has conventionally been thought to be particularly indicated in cases of bone loss to preserve skeletal length as noted, for example, in U.S. Pat. No. 5,571,103 to Bailey at col. 1, lines 35-43. However, such devices can be bulky, cumbersome, and or invasive to the user or patient. Further, the external fixation devices may not be suitable for use in soft osteoporotic bone.

In view of the foregoing, there remains a need for improved distal radius fracture treatment devices and techniques.

SUMMARY OF THE INVENTION

In a preferred embodiment, the present invention provides methods and devices for treating fractures in or adjacent the wrist and distal forearm. The present invention is particularly useful for stabilizing and treating distal radius fractures of a patient. The devices and methods of the present invention employs an intramedullary interlocking fixation rod (i.e, it interlocks the distal and proximal fracture fragments together) to stabilize the skeletal structure in a manner which can inhibit the amount of collapse or loss in skeletal length exhibited by a patient with a distal radius fracture. The devices and methods of the present invention may be especially useful for treating distal radius fractures in subjects with osteoporosis.

One aspect of the invention is a method for treating a distal radius fracture of a patient comprising the use of an internal fixation rod. As noted above, the radius anatomically has an articular joint surface, a metaphysis region, a shaft portion and a medullary canal associated therewith. The distal radius fracture has a fracture line which divides the radius into a distal fracture fragment portion and a proximal fracture fragment portion. The distal fragment portion includes the distal end of the radius proximate the articular joint surface, and the distal portion of the fracture has a width thereacross. The method comprises the steps of: (a) installing an elongated rod having opposing proximal and distal portions into the medullary canal of the patient such that the proximal portion of the rod resides above the fracture line (closer to the elbow) and the distal portion of the rod resides below the fracture line (closer to the hand); (b) securing a distal fixation member to the elongated rod and into the distal end portion of the radius at a location which is below the fracture line such that the distal fixation member extends internal of the patient substantially laterally across a portion of the width of the distal fracture fragment; and (c) anchoring the elongated rod inside the medullary canal of the radius at a location which is above (distal to) the fracture line.

Another aspect of the present invention is an internal fixation device for treating or repairing distal radius fractures having a fracture line forming distal and proximal fracture fragments. The radius is anatomically configured with a distal articular joint surface, a metaphysis region, a shaft, and a medullary canal. The anatomic position of the hand is palm forward or front such that the medial orientation is next to the body (fifth finger or ulna side of hand) and the lateral orientation is away from the body (thumb or radial side). Generally stated, the distal portion of the radius has a width which extends across (a major portion of) the arm from the medial side to the lateral side. The device includes an elongated fixation rod having opposing proximal and distal portions. The distal portion includes a head with a laterally extending distal aperture formed therein, and the proximal portion comprises at least one proximal aperture formed therein. The elongated fixation rod proximal portion is sized and configured such that, in position, it resides in the shaft inside a portion of the medullary canal of the radius of a patient. The device also includes a distal fixation member configured to enter the distal aperture and attach to the rod and the distal fracture fragment to hold the distal portion of the rod to the distal fracture fragment. The device further includes at least one proximal fixation member, a respective one for each of the at least one proximal apertures. The proximal fixation member is configured to secure the lower portion of the fixation rod to the radius at a position which is distal to the fracture line. In position, the elongated fixation rod is configured to reside within the radius, and the distal fixation member and the at least one proximal fixation member are configured to reside internal of the body of the patient.

In a preferred embodiment, the elongated fixation rod has a curvilinear profile. The curvilinear profile includes a distal curve portion at the distal portion of the device. The distal curve portion is adapted to accommodate the radial styloid region of the radius proximate the articular joint surface. The rod can also be provided as a plurality of segments matable or attachable. In one embodiment an intermediate segment can be provided in different lengths to allow for the adjustment of length according to a patient's anatomical considerations. Of course, the rod can be a unitary body provided in a number of standard sizes preferably statistically representative of the treatment population.

The foregoing and other objects and aspects of the present invention are explained in detail in the specification set forth below.

BRIEF DESCRIPTION OF THE DRAWINGS

FIG. 5A is a lateral view of an intramedullary rod configured to interlock or affix the bone fragments of a distal radius fracture according to one embodiment of the present invention.

FIG. 5B is a cross-sectional view of the rod shown in FIG. 5A taken along line 5B-5B.

FIG. 15A is an anterior-posterior view of the bone window shown in FIG. 14.

DESCRIPTION OF PREFERRED EMBODIMENTS

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. In the figures, certain layers, regions, or components may be exaggerated for clarity.

Figure 3A:
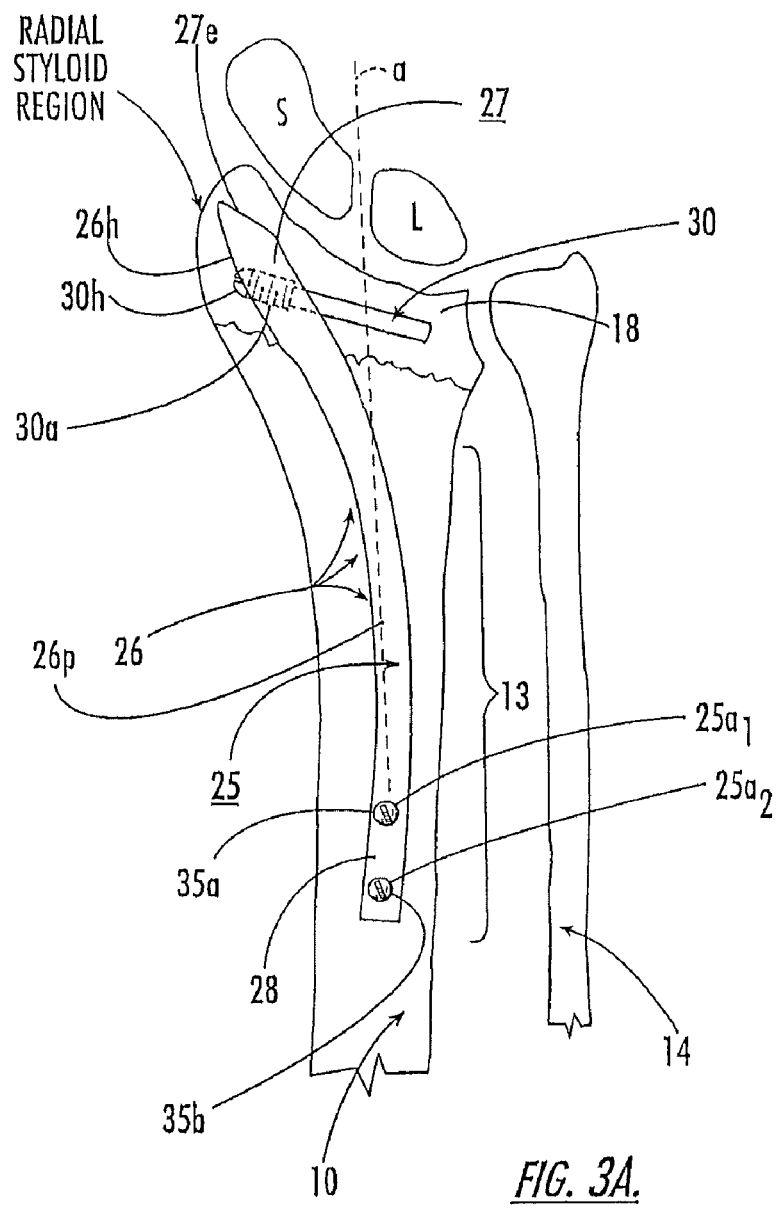
FIG. 3A is an anterior-posterior view of an intramedullary fixation rod attached to the radius for treating a distal radius fracture according to an embodiment of the present invention.

As shown in FIG. 3A, in a preferred embodiment, the intramedullary fixation device 25 includes an elongated axially extending rod 26 with a distal portion 27 and a proximal portion 28. The device 25 also includes a distal fixation member 30 and at least one proximal fixation member 35 (shown as two proximal fixation members 35a, 35b). The rod 26 includes a head 26h at the distal end portion 27 of the rod 26. A distal aperture 30a is formed into the head 26h of the distal portion such that it extends across the width of the rod 26.

As shown, the distal fixation member 30 is configured to enter and extend through and beyond the distal aperture 30a to engage with the distal fracture fragment 18 and secure the rod 26 and the distal fracture fragment 18 theretogether. Preferably, the distal fixation member 30 is sized to extend across a major portion of the width of the distal fracture fragment 18. More preferably, the distal fixation member 30 is sized with a length which is sufficient to extend across substantially all of the fracture fragment 18 so as to provide support for the radial, center, and ulna aspects of the distal fracture fragment 18 (the ulna aspect being the part of the fracture fragment adjacent or proximate the ulna 14 while the radial aspect being the portion of the fracture fragment on the opposing side of the view shown in FIG. 3A and the center aspect being the portion in between).

Figure 3B:
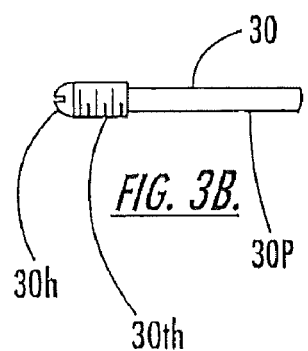
FIG. 3B is an exploded view of the distal fixation attachment member shown inserted into the fixation rod in FIG. 3A according to one embodiment of the present invention.

FIG. 3B illustrates the distal fixation member 30 apart from the rod 26. The distal fixation member 30 can be configured as any suitable attachment means to secure the distal fracture fragment 18 to the rod 26, while also providing lateral structural reinforcement. For example, but not limited to, the attachment means can be one or more of a pin, nail, threaded or partially threaded member such as a screw, or a combination of the above. FIG. 3B illustrates the distal fixation member 30 as having, in serial order, from one end to the other, a head portion 30h, a threaded portion 30$_{th}$, and a pin portion 30p.

Figure 6:
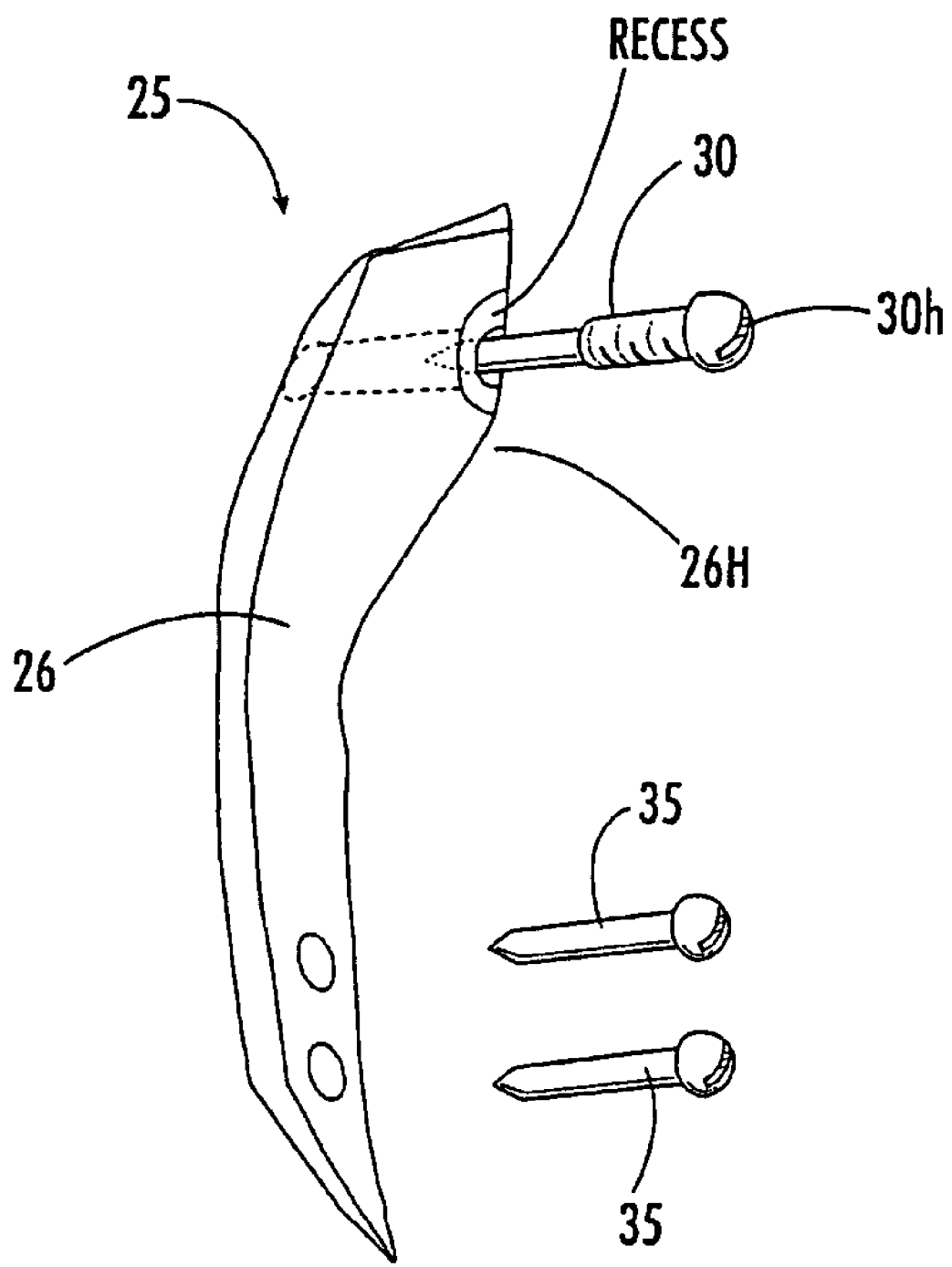
FIG. 6 is a perspective view of an intramedullary fixation device according to one embodiment of the present invention.
Figure 7:
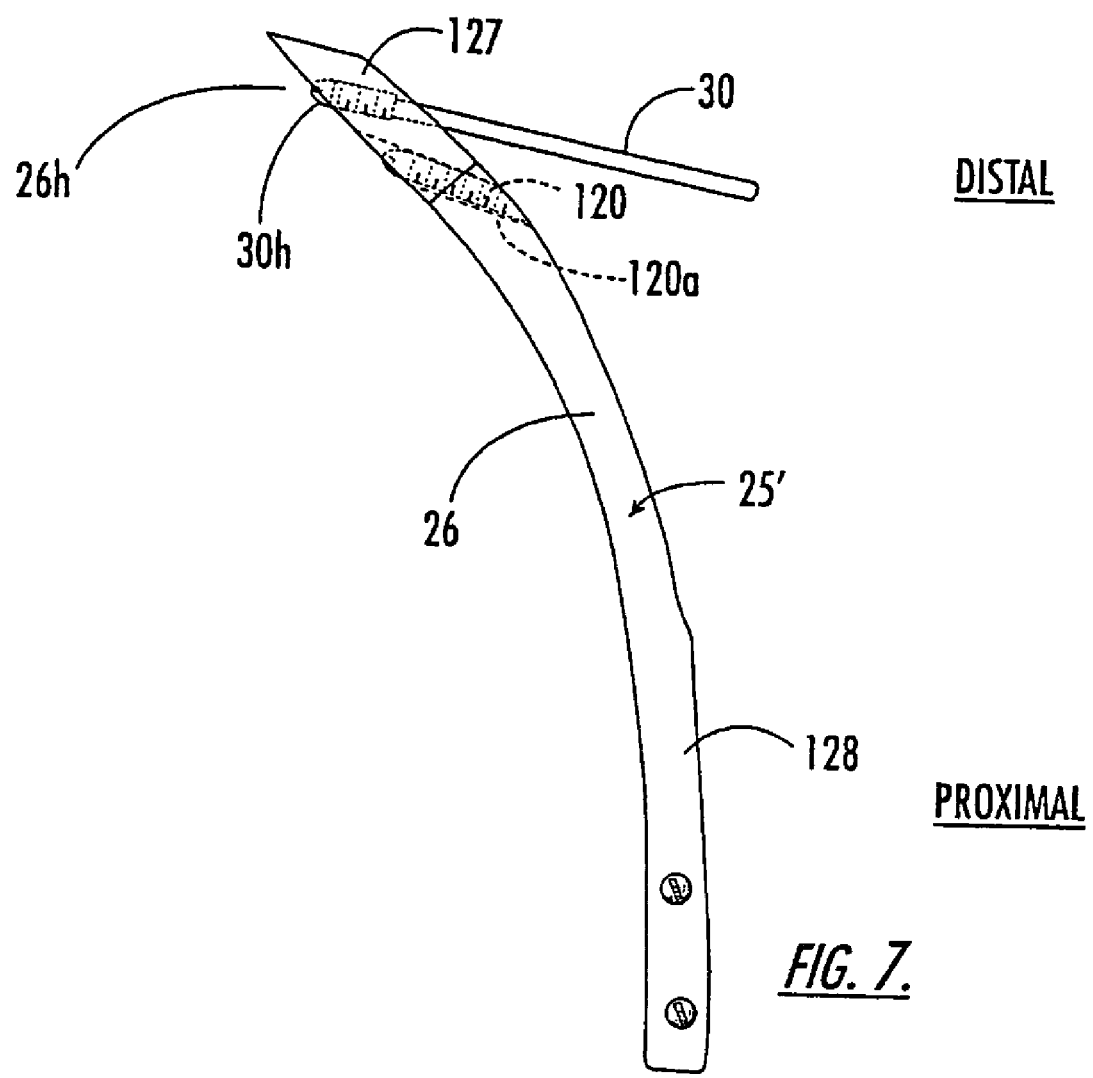
FIG. 7 is a side view (shown oriented anterior to posterior) of an alternate embodiment of an intramedullary system according to the present invention.

In one embodiment, as shown in FIG. 3A, the head of the distal fixation member 30h extends beyond the edge of the body of the rod 26. However, as schematically shown in FIG. 7, the aperture 25a can be configured (such as with a countersunk or recessed portion configured with a depth sufficient to receive the head 30h, therein) such that upon assembly, the distal fixation member head 30h is substantially flush or recessed with the outer contour or profile of the rod 26. FIG. 3A also illustrates that, in position in the patient, the distal fixation member 30 is preferably configured to directly abut the outer surface of the rod 26. FIG. 6 is a perspective view of one embodiment of the intramedullary fixation device 25. This embodiment shows that the rod 26 is configured as a unitary body with a recess to receive the head 30h of the distal fixation member 30.

Figure 1:
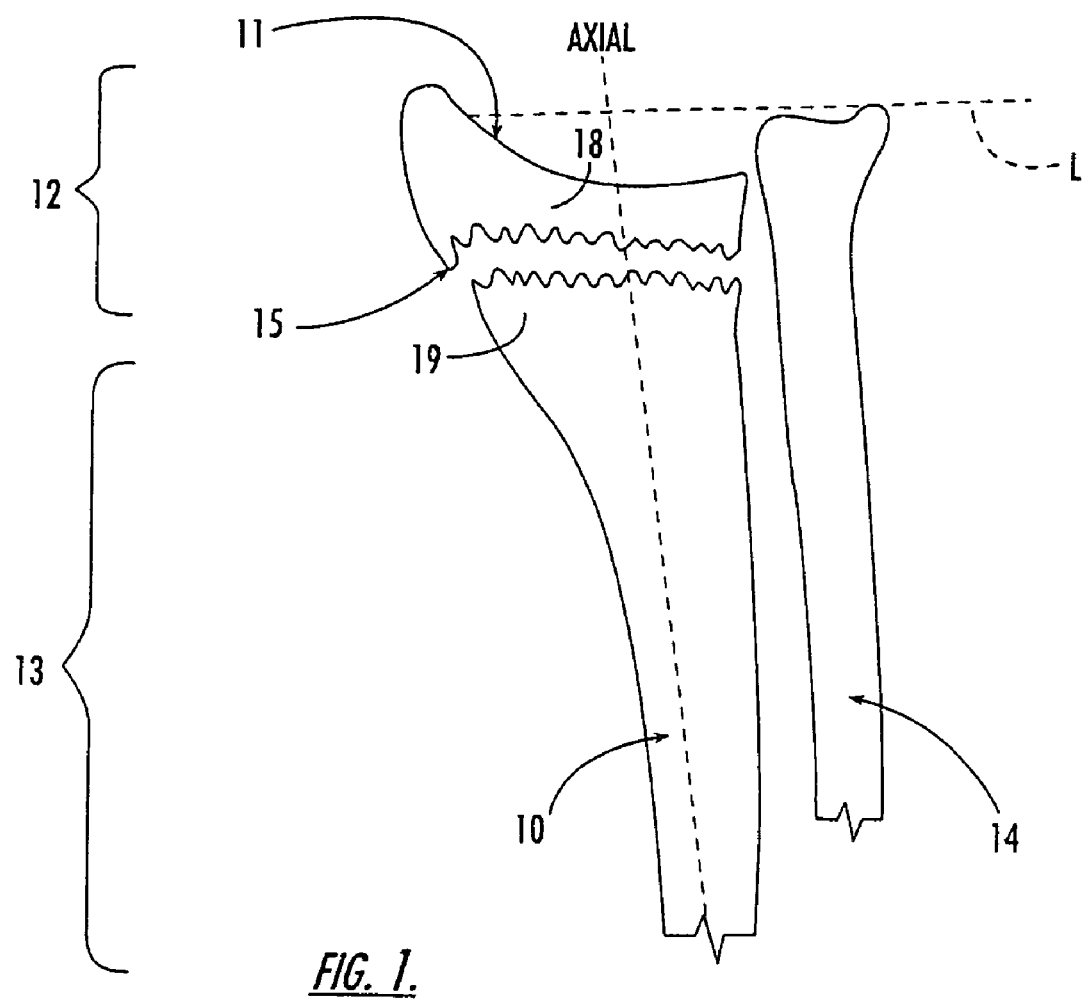
FIG. 1 is an anterior-posterior view of a distal radius fracture illustrating a fracture line proximate the articular joint surface.
Figure 2:
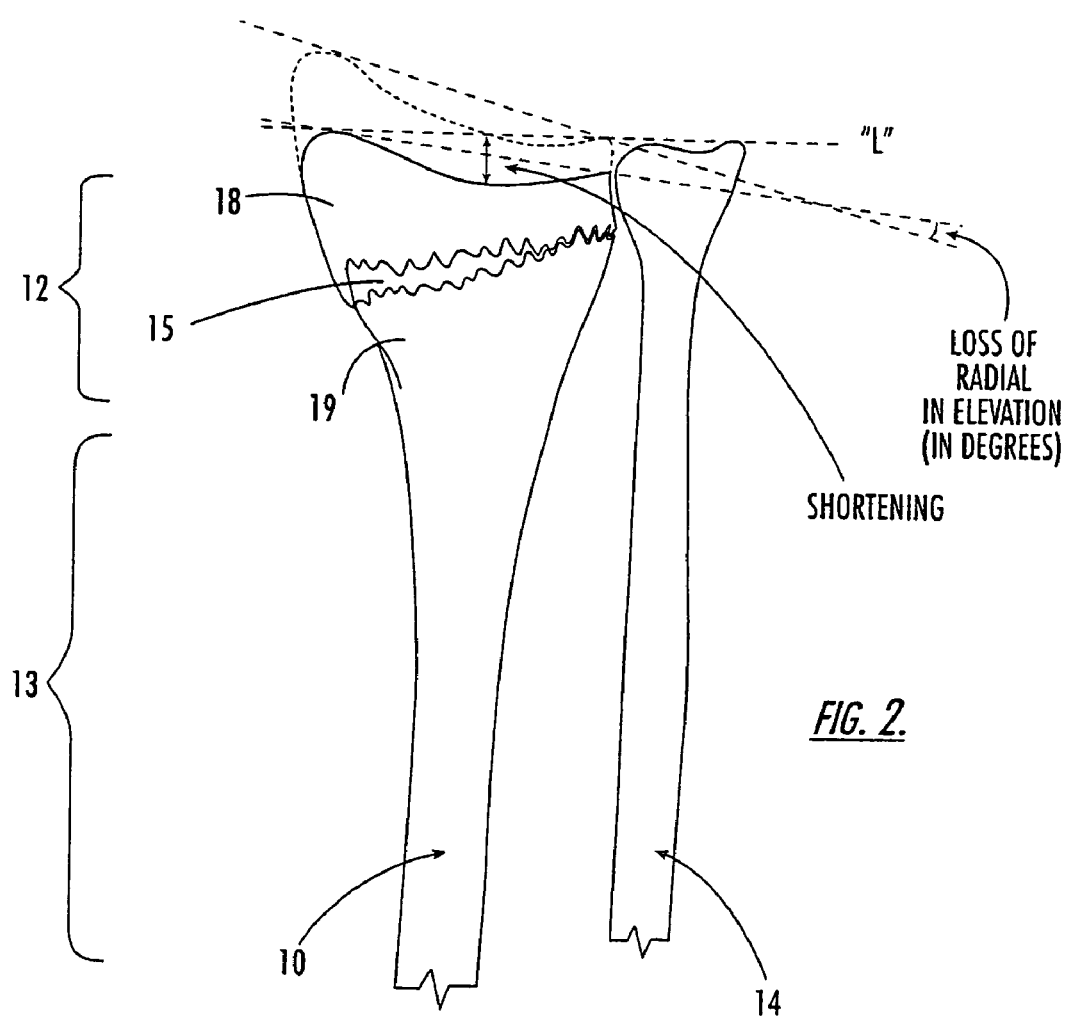
FIG. 2 is an anterior-posterior view of a distal radius fracture similar to that shown in FIG. 1. This figure illustrates an alternatively configured fracture line proximate the articular joint surface.
Figure 4:
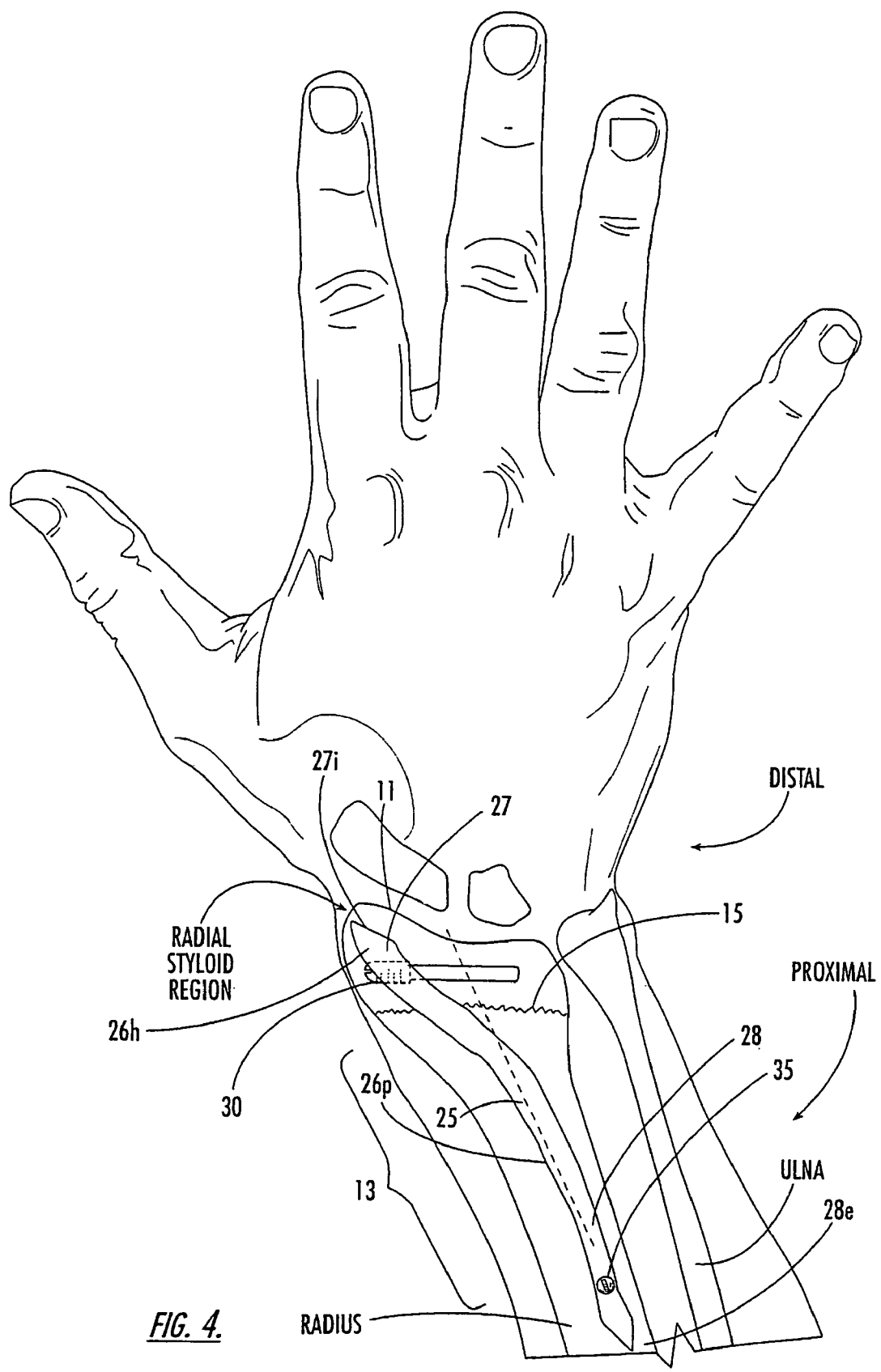
FIG. 4 is a front schematic view of the distal fixation rod of FIG. 3A in position as an internal fixation device held within the body of the patient according to one embodiment of the present invention.

In a preferred embodiment, the rod 26 is configured with a profile 26p which is curvilinear when viewed from the anterior-posterior view, as shown, for example, in FIGS. 3A and 4. As shown, the proximal portion of the rod 28 is substantially linear and is configured to axially extend within the medullary canal of the patient in the radial shaft. As the rod 26 approaches the metaphysis region (12, FIG. 1) it gradually curves from the substantially linear axial extending portion so as to position the distal end 27e of the rod 26 proximate the radial styloid region of the distal radius. Preferably, the rod 26 is configured to follow the contour line of the radius as it transitions from the proximal portion 28 having a substantially linear contour in the shaft region to the distal portion 27 which has a curvilinear or slight arcuately contoured shape proximate the metaphysis region.

FIGS. 3A and 4 also illustrate that the head 26h of the rod 26 is preferably configured with a body which has an increased perimeter or area size with respect to the proximal 28 portion of the rod 26. It is also preferred that the distal end of the head 26h be beveled or inclined 27i. As shown, the tip or end of the head 26h slopes downwardly from the side surface adjacent the radial portion toward the ulna aspect of the fracture fragment 18.

It is additionally preferred that the distal aperture 30a be formed in the rod 26 such that it allows the distal fixation member 30 to extend therethrough and reside at a position which is angularly offset from the axial axis. As shown in FIG. 3A, the axial axis is coincident with the centerline of the proximal portion of the rod (indicated by the letter "a" in FIG. 3A). Preferably, the distal fixation member 30 extends at a position which is less than about ninety degrees, and preferably between about 10 degrees to less than about 90 degrees, away from the axial axis, such that it is approximately in-line with the articular surface.

In this embodiment, the head 26h of the rod 26 can buttress the distal radius region and increase the structural effectiveness of the rod. Thus, together with the proper positioning of the distal portion 27 of the rod 26 in the distal radius and/or the medial extension of the distal fixation member 30, the head 26h, can reinforce or positively affect the structural integrity of the device to help support the radial styloid region of the distal fracture fragment.

Referring again to FIG. 3A and FIG. 4, at least one, and preferably two or more, proximal fixation members 35 are used to secure the rod 26 to the shaft region 13 of the radius 10 at the lower or proximal portion of the rod 26. FIG. 3A illustrates the use of two similarly sized proximal fixation members 35a, 35b, respectively, while FIG. 4 illustrates the use of one 35. Preferably, as shown in FIG. 5A, the proximal fixation members 35a, 35b are respective self-tapping screws positioned on the rod 26 such that they are proximate to each other. However, pins, nails, or other attachment means (as well as numbers and positioning of same) can also be used as will be appreciated by one of skill in the art. It will be appreciated, by those of skill in the art, that the proximal fixation members 35 and corresponding apertures 25a are primarily used to inhibit shortening of the skeletal structure. As shown in FIG. 5A, the proximal fixation member 35 transversely extends in serial order, through a portion of the radius shaft, through a corresponding proximal receiving aperture 25a formed in the rod 26, and then into an opposing portion of the radius shaft to thereby secure or locate and hold the proximal portion of the rod 25 relative to the radius, the proximal fixation member having a length and opposing ends sized and configured accordingly 36, 38.

FIG. 4 schematically illustrates the preferred post-operative position of the intramedullary fixation device 25 in the patient. That is, post-operatively in position in the patient, the rod 26 and distal and proximal fixation members 30, 35 are held within the body of the subject such that the device 25 is an internal fixation device and is devoid of externally located coupling or fixation members.

As shown in FIG. 4, the rod 26 is installed into the medullary canal of the patient such that the distal portion 27 of the rod 26 resides distal to the fracture line 15 (but substantially within the distal radius, preferably so as to reside proximal to the articular joint surface 11) and the bottom or proximal portion 28 of the rod 26 extends through and resides proximal to the fracture line 15. The distal fixation member 30 is secured to the rod 26 and to the distal end portion of the radius at a location which is distal to the fracture line 15 in the metaphysis region of the distal radius. As is also shown, the distal fixation member 30 extends (to reside internal of the body of the patient) substantially transversely across a portion of the width of the distal fracture fragment 18. The device 25 may not be preferred for use with comminuted distal radius fractures.

In position, the rod 26 is configured such that it also extends through a portion of the medullary canal to terminate therein in the shaft region 13 of the radius 10 (FIG. 1) (at a location which is proximally spaced away from the fracture line 15). The proximal portion 28 of the rod 26 is anchored to the radius so as to reside inside the medullary canal of the radius. The proximal portion 28 of the rod 26 is fixed in position relative to the shaft of the radius by the use of at least one pin, screw, or the like, as discussed above. As is also noted above, it is more preferred that two (and potentially three or more) to provide increased structural stability so as to inhibit the propensity of the rod 26 to toggle or move distally with the distal fragment.

FIG. 4 also illustrates that the proximal end of the rod 28*e* may be configured with a reduced cross-sectional size or tapered perimeter relative to the portion of the rod 26 thereabove to allow for ease of insertion into the patient. Preferably, as shown, the proximal end of the device 28*e* is substantially pointed.

FIG. 5A illustrates the rod 26 with a length "L", a width "W" and a thickness "T". It is envisioned that the rod 26 be provided or be made available for use in a plurality of lengths and widths so that the clinician can select the appropriate dimensions according to the particular anatomical needs of the patient. Preferably, for the distal radius fracture, the length of the rod 26 is between about 2-5 inches long, and more preferably between about 2.5 inches-4.0 inches long. It is also preferred that the width of the rod 26 be provided in an arrangement of incremental sizes. It is thought that suitable widths may be between about 2-8 mm in width and more preferably between about (2.5-4 mm) in width.

As shown in FIG. 5B, the rod 26 is held in the medullary canal of the radius of the patient. The lower or proximal portion 28 of the rod 26 is preferably held substantially centrally in the shaft portion 13 of the radius 10. In one embodiment, the cross sectional shape of the rod 26 is rectangular. The rod 26 can be configured with other cross-sectional shapes, such as, but not limited to, circular, oval, square, triangular, and hexagon. It is also preferred that in designs with sharp edges, that the edges be radiused ("break edges") to reduce the likelihood of stress fractures in the rod 26 (or in the bone adjacent the rod). Further, the distal portion 27 of the rod 26 may have a different cross-sectional shape and configuration from the proximal portion 28 of the rod 26. For example, the proximal portion 28 of the rod 26 may have a circular shape with the addition of a ribbed portion on one side to inhibit rotation once in the intramedullary canal in the radius of the patient, while the distal portion 27 of the rod 26 can have an oval or rectangular shape (not shown).

FIG. 7 illustrates another embodiment of an intramedullary fixation device 25' according to the present invention. In this embodiment, the rod 26 is configured as first and second attachable segments or links 127, 128. As shown, the distal segment 127 of the rod 26 is configured with the head of the rod 26*h* while the proximal portion 128 is again configured to reside in the medullary canal of the radius shaft. The two segments 127, 128 are configured to align and mate together to define the rod 26. As shown in FIG. 7, a linking screw 120 is inserted into a threaded aperture 120*a* that it spans the first and second segments 127, 128 when aligned. Of course, other attachment means or segment link configurations can also be used, such as, but not limited to, bayonet type fittings, friction fit or threaded matable female/male components, and the like.

Figure 8:
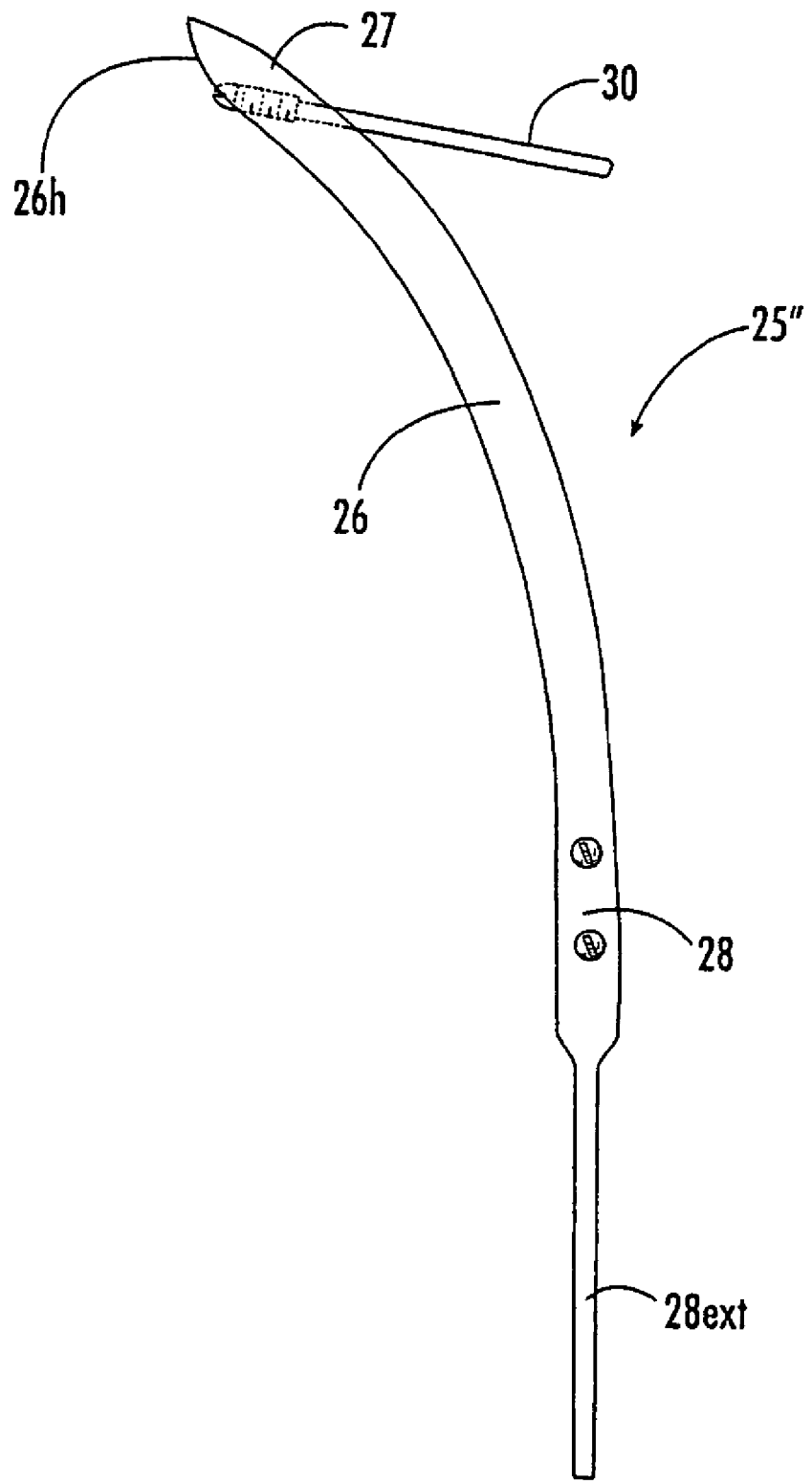
FIG. 8 is a side view (shown oriented anterior to posterior) of another embodiment of an intramedullary system according to the present invention.

FIG. 8 illustrates another embodiment of an intramedullary fixation device 25" for the radius according to the present invention. In this embodiment, the rod 26 includes a proximal extension 28*ext*. As shown, the proximal extension 28*ext* is tapered adjacent the proximal end portion 28 of the rod 26. The extension 28*ext* is configured to reside in a more proximal portion of the radius shaft (away from the hand and closer to the elbow). This embodiment may also be used in the absence of a distal radius fracture to treat proximal radius fractures. FIG. 8 also illustrates that the distal fixation member 30 is oriented at about 45 degrees with respect to the axial axis. In any event, this configuration can allow for additional support in the shaft region of the radius (i.e., more proximal "purchase").

Figures 9A, 9B:
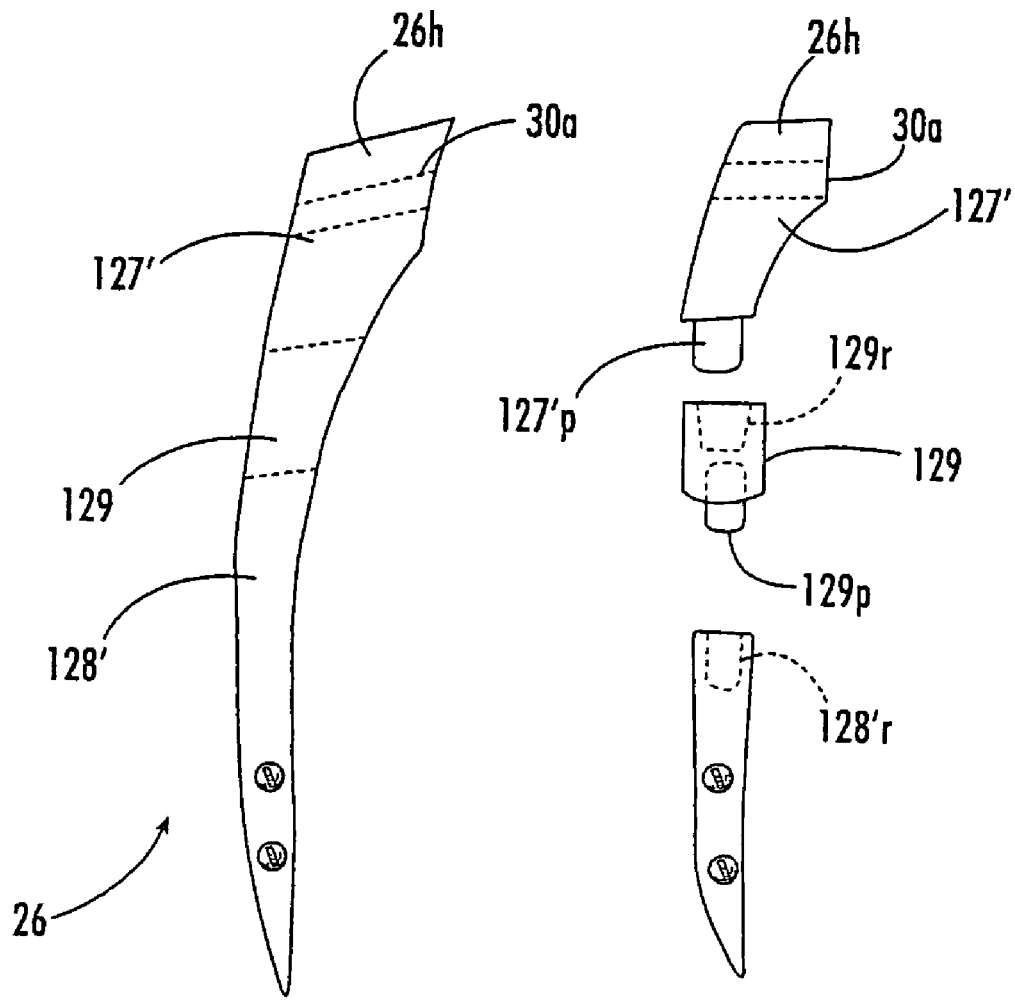
FIG. 9A is a front anterior-posterior view of an alternate embodiment of a distal fixation rod according to the present invention.
FIG. 9B is an exploded view of the linked or multi-segment rod shown in FIG. 9A.

FIG. 9A illustrates a rod 26 having a body with multiple segments or links 127', 129, 128'. As shown, in this embodiment, the rod 26 is defined by three segments, the distal segment 127', an intermediate segment 129, and a proximal segment 128'. FIG. 9B illustrates that, in this embodiment, the distal segment 127' includes a protrusion 127*p'* while the upper portion of the intermediate segment 129 includes a recess 129*r* configured and sized to matably and/or securely receive the protrusion 127*p'* therein. Similarly, the proximal segment 128' includes a recess 128*r'* formed therein configured to receive the intermediate segment protrusion 129*p* therein. Preferably, the segments 127', 129, 128' are sized and configured to be held together by a frictional fit of the interlocking or mating components, however, a biocompatible adhesive can also be used, as desired. Other attaching means can also be used to secure the segments together as will be appreciated by those of skill in the art. For example, the protrusion 127*p'* can be threaded and configured to threadably engage with a threaded recess 129*r* formed in the upper portion of the intermediate segment 129. Similarly, the proximal recess 128*r'* can be threaded and configured to threadably engage with the intermediate segment 129*p* protrusion (which can be configured as a correspondingly-configured male threaded component).

Figure 9C:
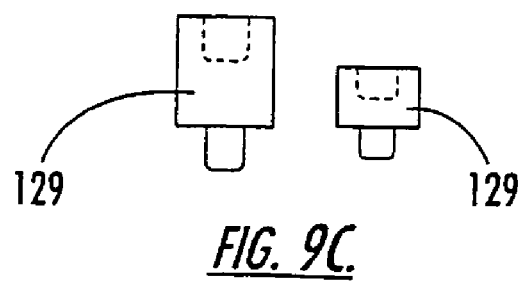
FIG. 9C is a front view of a set of intermediate rod segments according to an embodiment of the present invention.

As shown in FIG. 9C, the intermediate segment 129 can be provided in an assortment of lengths to allow the rod 26 to be adjusted to a desired length according to the anatomical considerations of the patient. Alternatively, the intermediate segment 129 can be a plurality of similarly sized or different, incrementally sized segments. In this way, the distal and proximal segments 127', 128' can be provided as standardized-length components with the intermediate segment 129 providing an adjustable length. Thus, the clinician can custom fit the rod 26 at the use site. That is, the clinician can assess the patient and then determine the appropriate number or size of intermediate segments 129 to be used dependent on the length desired. This custom fit does not require the use of a preformed rod or a special order rod. Rather, the fit can be carried out at the clinic, use, or installation site (proximate in time or contemporaneous with the treatment) to fit the number and size components together according to the needs of the patient. Alternatively, the distal and/or proximal segments 127', 128' can also (or alternatively) be configured as or provided in different lengths.

Figure 10:
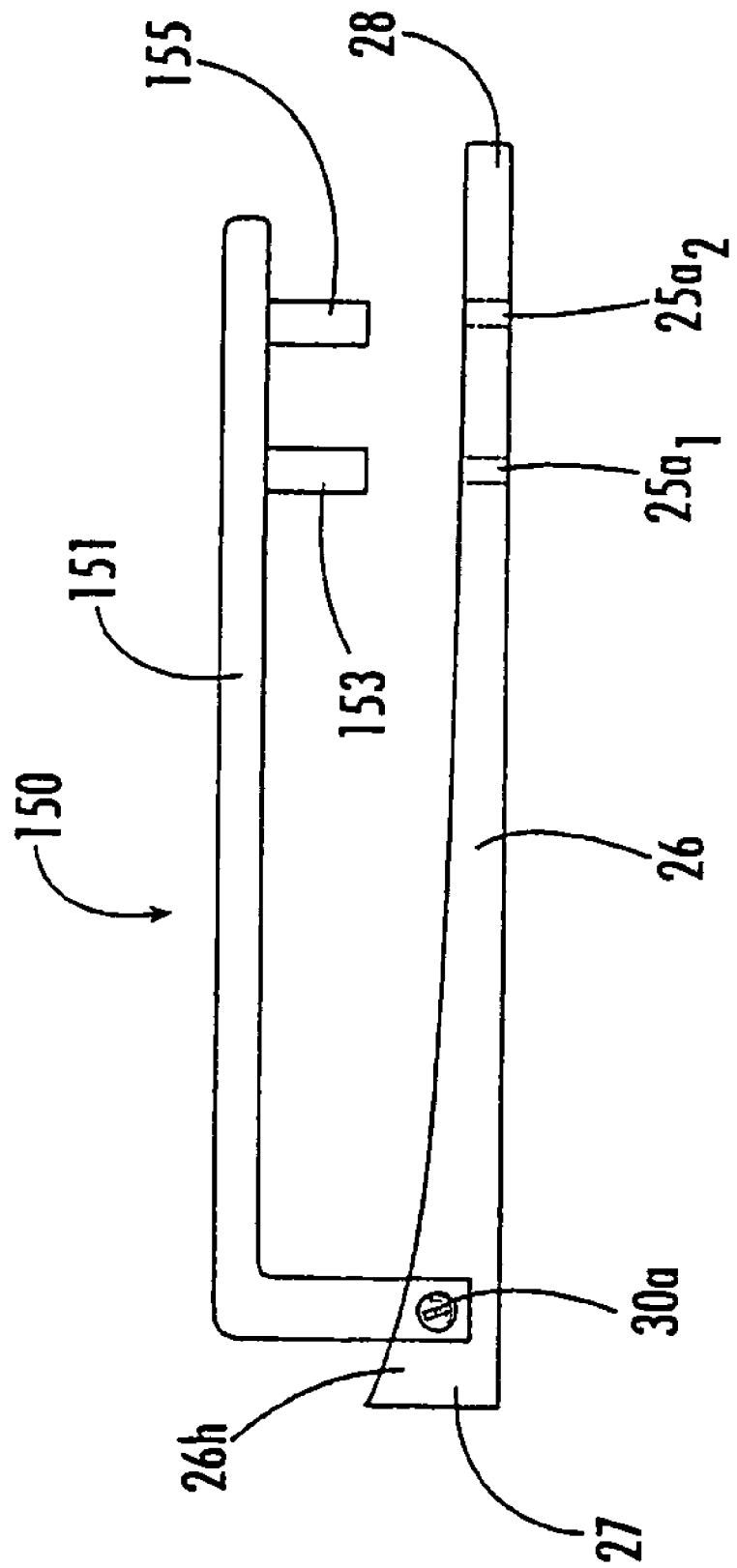
FIG. 10 is a schematic side view of an intramedullary system with an external detachable positioning guide according to an embodiment of the present invention.

FIG. 10 illustrates the use of an insertion or positioning guide 150 affixed to the distal end portion 27 of the rod 26 to allow for ease of insertion and placement into the patient. As shown, the guide 150 includes an axially (or longitudinally)

extending arm 151 which is configured to reside external of the body of the patient when the rod 26 is inserted into the intramedullary canal. As is also shown, the guide arm 151 includes a visual locating means or visual indicia 153, 155 which correspond to the proximal fixation apertures $25a_1$, $25a_2$ to mark or identify the location of the internal apertures when the rod 26 is in a desired position in the patient. This allows the physician to be able to insert the proximal fixation members 35a, 35b in the proper location, aligned with the proximal apertures on the rod 26 held inside the patient.

As shown, the visual indicia 153, 155 is preferably provided as laterally extending drill guides 153, 155 which act to support a drill as it enters the patient and allows the drill to be inserted therein and guided to the desired location to provide bores into the bone on opposing sides of the rod 26 that are aligned with the rod proximal fixation apertures $25a_1$, $25a_2$.

Figure 12:
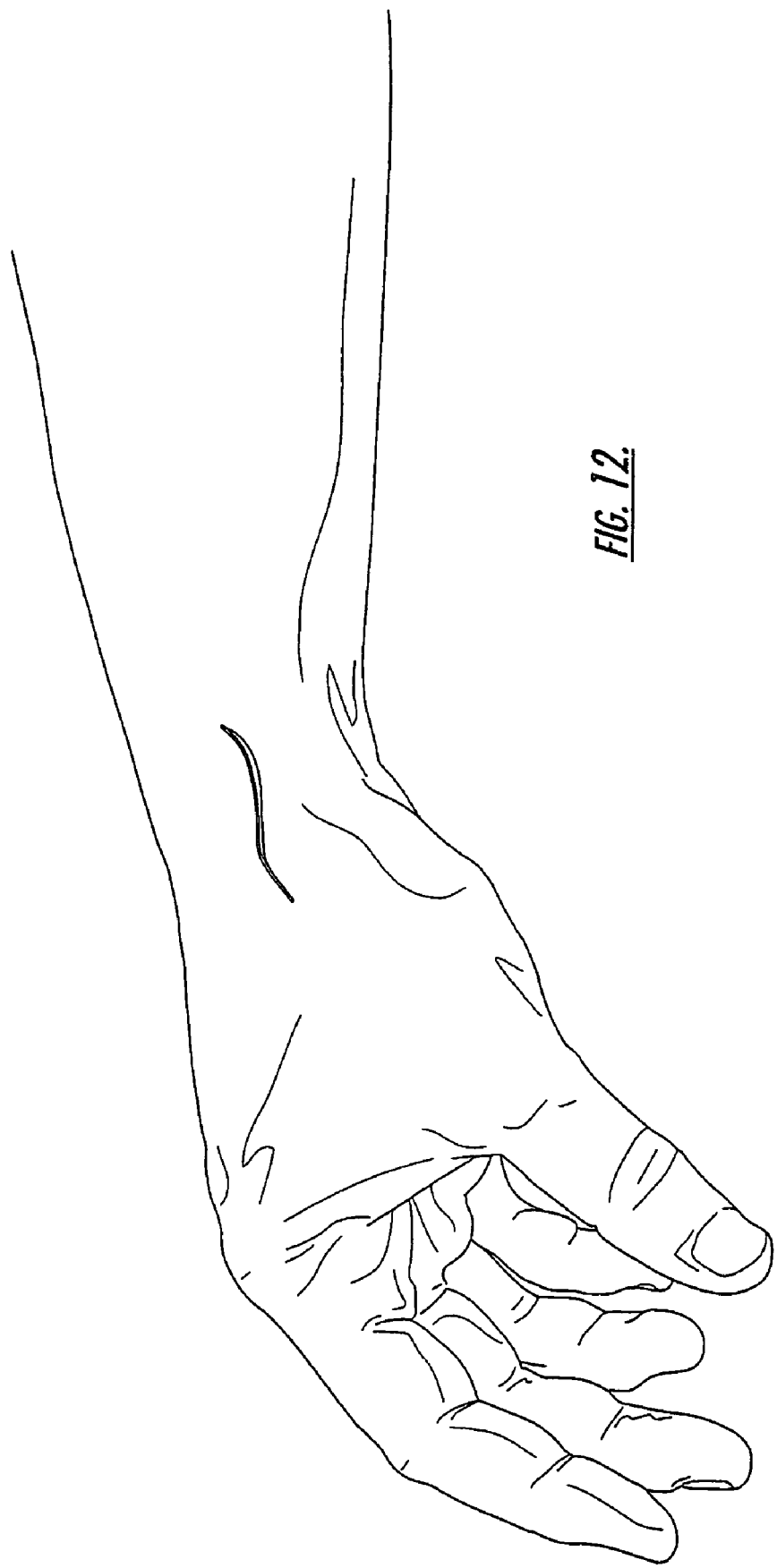
FIG. 12 is perspective view of the arm of a patient illustrating a sigmoid or longitudinal incision over the radial styloid area.
Figure 13:
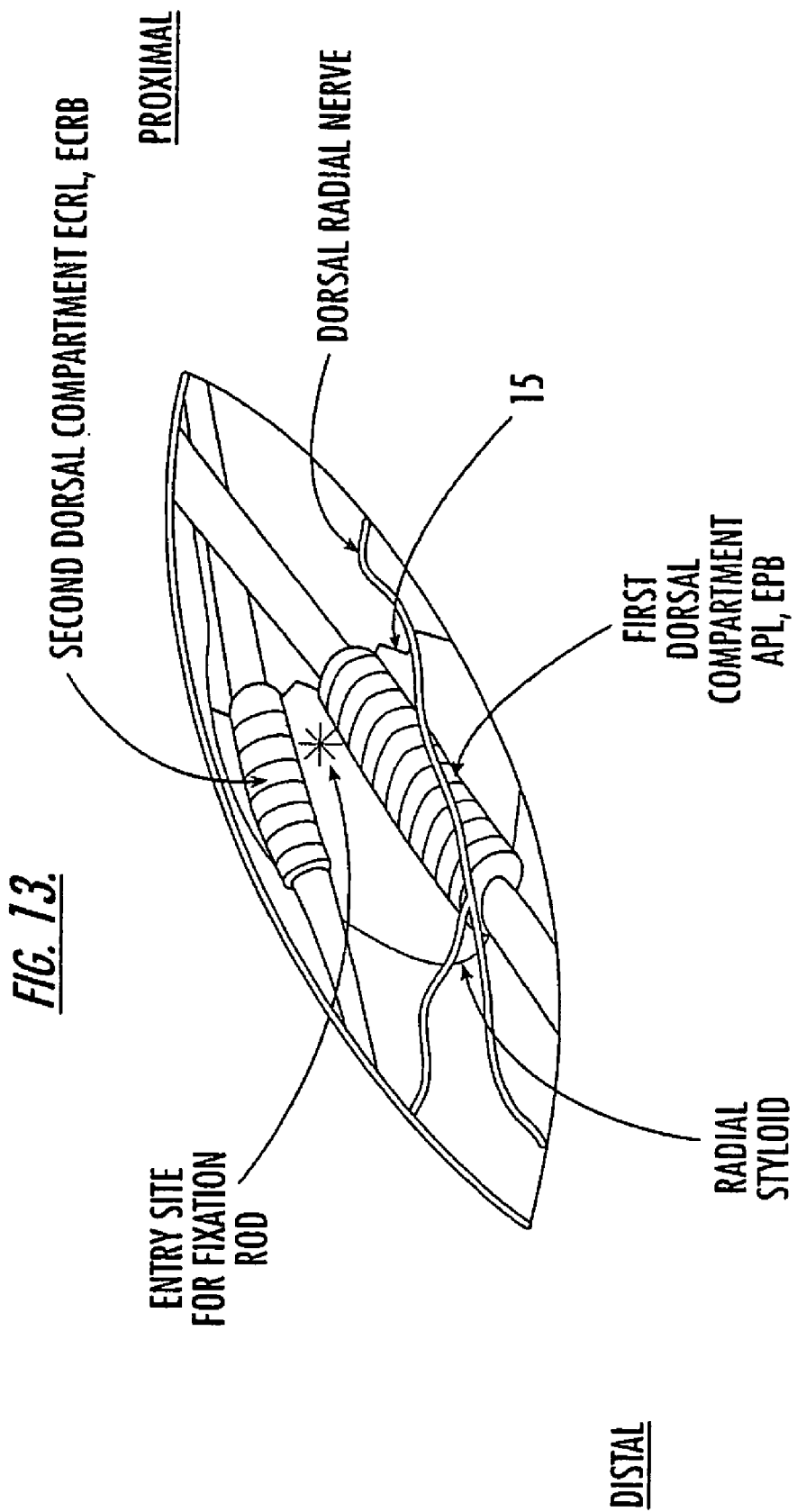
FIG. 13 is an enlarged schematic view of the incision site in the patient shown in FIG. 12 to illustrate preparation of the site for positioning intramedullary fixation rods for distal radius fractures according to an embodiment of the present invention.
Figure 14:
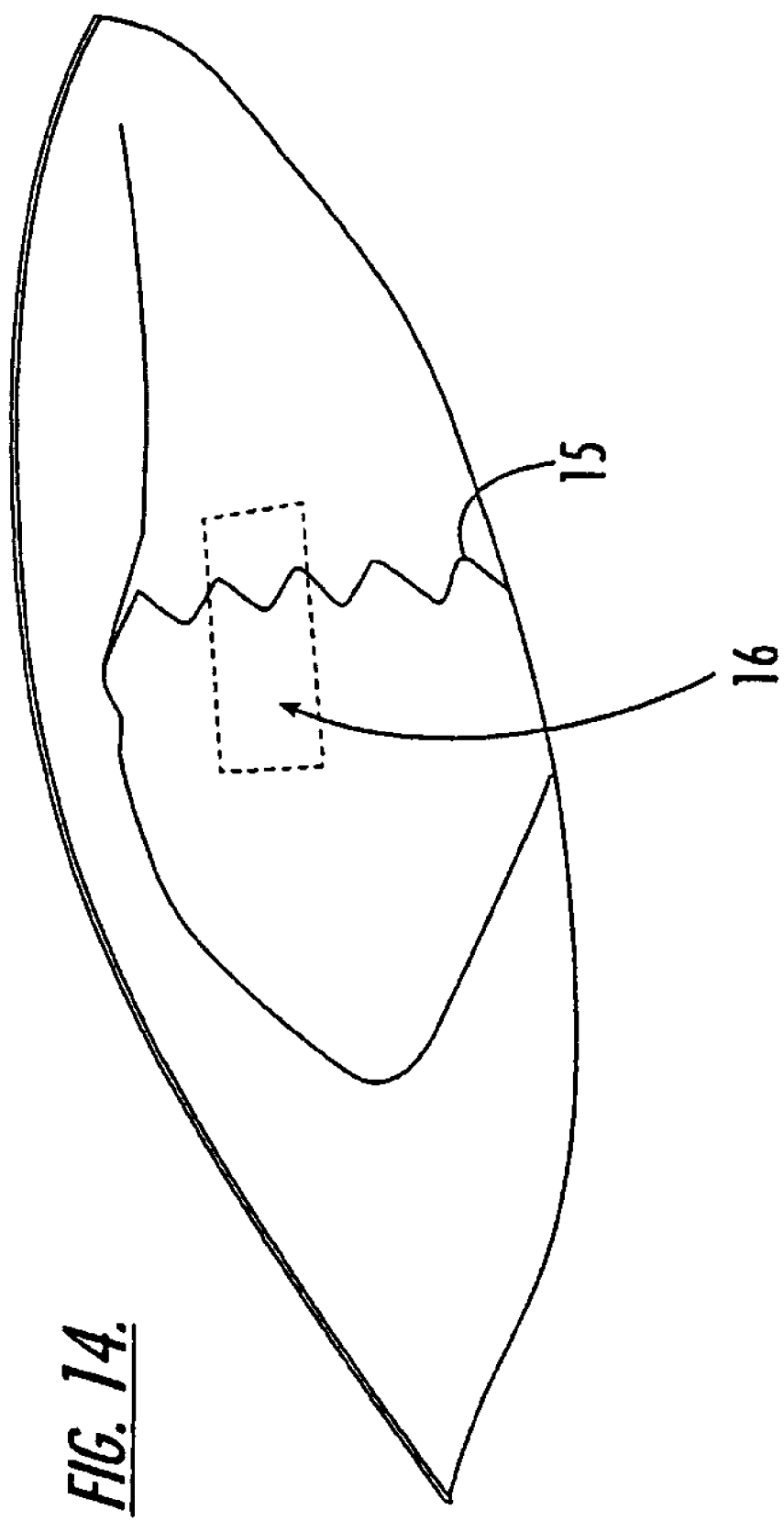
FIG. 14 is an enlarged schematic view of the incision site shown in FIG. 13 illustrating that a small bone window may be made or formed into the radius such that it extends across the fracture site according to the present invention.

Referring to FIG. 12, generally described, to position the intramedullary fixation rod 26 into the patient, an incision is made, such as a sigmoid or longitudinal incision over the radial styloid region of the patient's arm (adjacent to the base of the thumb). As shown in FIG. 13, dissection is carried down to the interval between the first and second dorsal compartments. Care should be taken so as not to injure the branches of the dorsal radial nerve. A small area of exposed bone is present between the first and second compartments (typically covered only by periosteum). As shown in FIGS. 14 and 15A, a small bone window 16 is preferably formed or made into the radius in this area. It may be appropriate to elevate the sheaths of the first and second dorsal compartments to facilitate adequate exposure for the bone window 16. Although shown as a substantially rectangular bone window, other shapes may also be used to provide access to the fracture region.

Figure 15B:
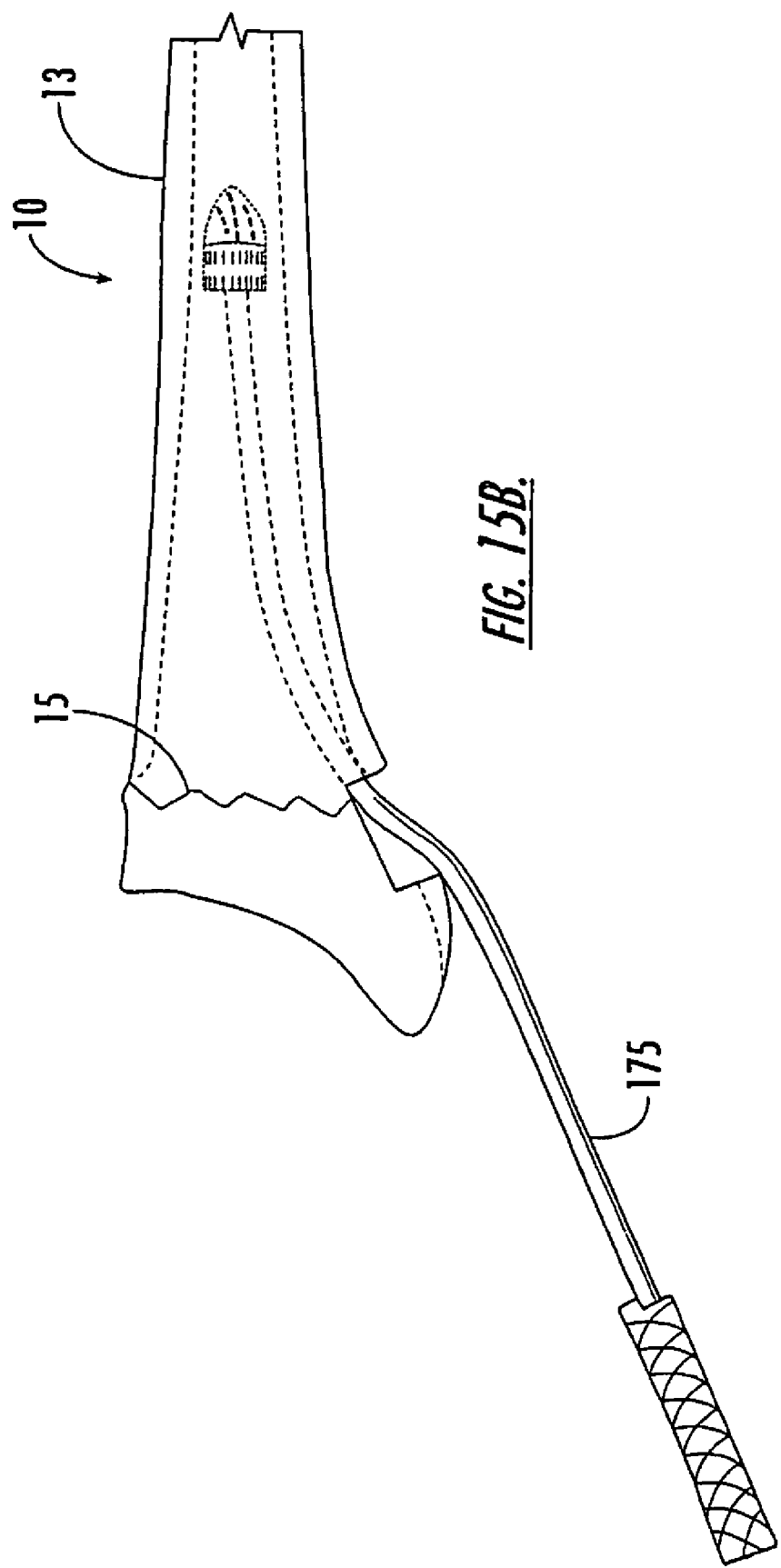
FIG. 15B is a schematic view of the prepared bone site shown in FIG. 15A illustrating the use of a sound or broach instrument which is sized and configured to be inserted into the intramedullary canal of the radius to determine size and/or open or prepare the canal to receive a fixation rod according to an embodiment of the present invention.

As shown in FIG. 15B, a finder, sound, or broach-like device 175 can be used prior to inserting the fixation rod 26 into the patient. The device 175 is preferably semi-flexible to follow the contour of the canal in the radius. The device 175 can be inserted through the bone window 16 and about the fracture region and used to determine the size and length of the intramedullary canal and/or to open the canal to a size suitable for receiving the fixation rod 26. The sounds are available in length- and width calibrated sizes to help determine a size and length suitable for the fixation rod 26 according to the particular patient's intramedullary canal structure. As such, the device 175 can bore out or ream and/or define a desired entry and insertion passageway for the device 25, 25', 25" in advance of an actual installation into the patient. A fluoroscopic evaluation technique can be used to visualize the insertion of the device 175 and can help determine if the canal needs to be enlarged with a reamer or if a insertion path needs to be formed or shaped.

After the appropriate size and length fixation rod 26 is selected, the rod can be attached to an insertion guide device 150, 150'. FIG. 10 illustrates one embodiment of a guide 150. As shown, an applicator/handle or driver 150 is attached to the rod 26 into the distal aperture 30a. The handle or driver 150 then allows the physician to insert and guide the rod 26 into the desired location in the medullary canal in the radius. Once the head 26h of the rod 26 is positioned below the articular joint surface, in its desired location in the distal radius, the proximal fixation members 35 (35a, 35b) are ready for insertion. Preferably, a small incision (or two) is made at the proximal site of the radius. A drill or driver is inserted into the locator or drill guide holder 152 to align the entry of the proximal fixation member about the proximal aperture 25 and then force the threaded proximal fixation member(s) 35 (35a, 35b) through the bone on the first (dorsal) side of the shaft of the radius, through the rod aperture $25a_1$ ($25a_2$) and into the bone on the opposing (volar) side of the radial shaft. Preferably, the proximal fixation member 35 (35a, 35b) extends through both sides of the bone. Next, the guide 150 shown in FIG. 10 is removed and the distal fixation member 30 is then inserted into the rod 26 through the distal aperture 30a and attached to the distal radius (FIG. 4). Preferably, the distal fixation member 30 is inserted into the radius at the fracture site or at an exposed site (created by removing a portion of the bone) to allow the head 30h (FIG. 3A) of the distal fixation member 30 to be inserted into the rod 26 such that it rests directly against the body of the rod 26 (either protruding, flush, recessed therewith) and extends into the distal fracture fragment 18.

Figure 16:
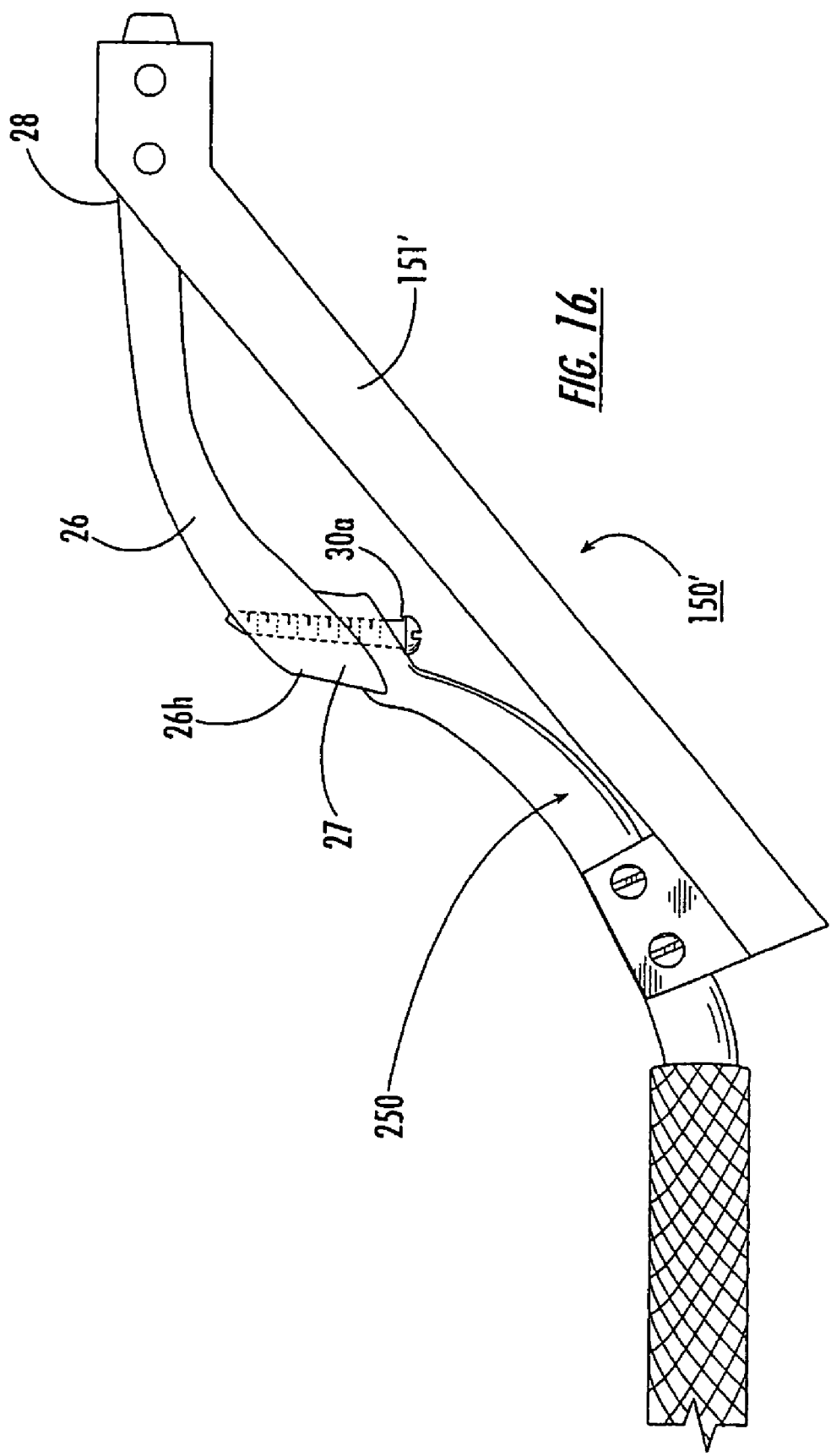
FIG. 16 is a top anterior-posterior view of an intramedullary fixation rod assembled to a rod driver and screw attachment guide according to one embodiment of the present invention.
Figure 17:
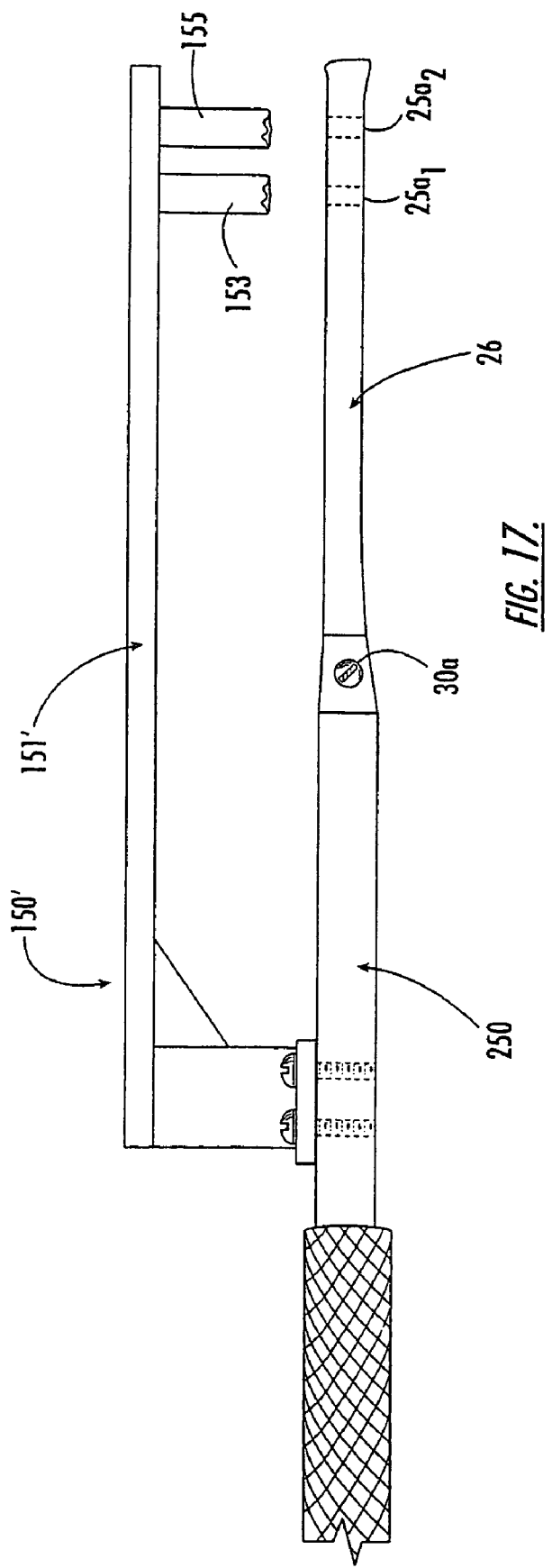
FIG. 17 is a side (lateral) view of the device shown in FIG. 16.

FIGS. 16 and 17 illustrate an additional embodiment of an insertion guide 150'. In this embodiment, the device 150' includes a rod driver 250 and an interlocking screw attachment guide 151'. Once the proper rod size is identified, the rod 26 is attached to the rod driver 250. The rod driver 250 is attached to the fixation rod 26 via the distal aperture in the head of the rod 26 and an associated attachment member (shown as a screw 30a) and the interlocking screw attachment guide 151' is attached to the rod driver 250. As for the other guide embodiment described above, the interlocking screw attachment guide 151' provides a screw guide alignment means such as screw or pin portals 153, 155 to facilitate proper orientation and location of the proximal screws or pins into the patient and into the shaft 25 of the fixation rod 26. Thus, in this embodiment, the span of the screw attachment guide 151' is configured to provide the proper alignment position relative to the rod driver 250.

Figure 18:
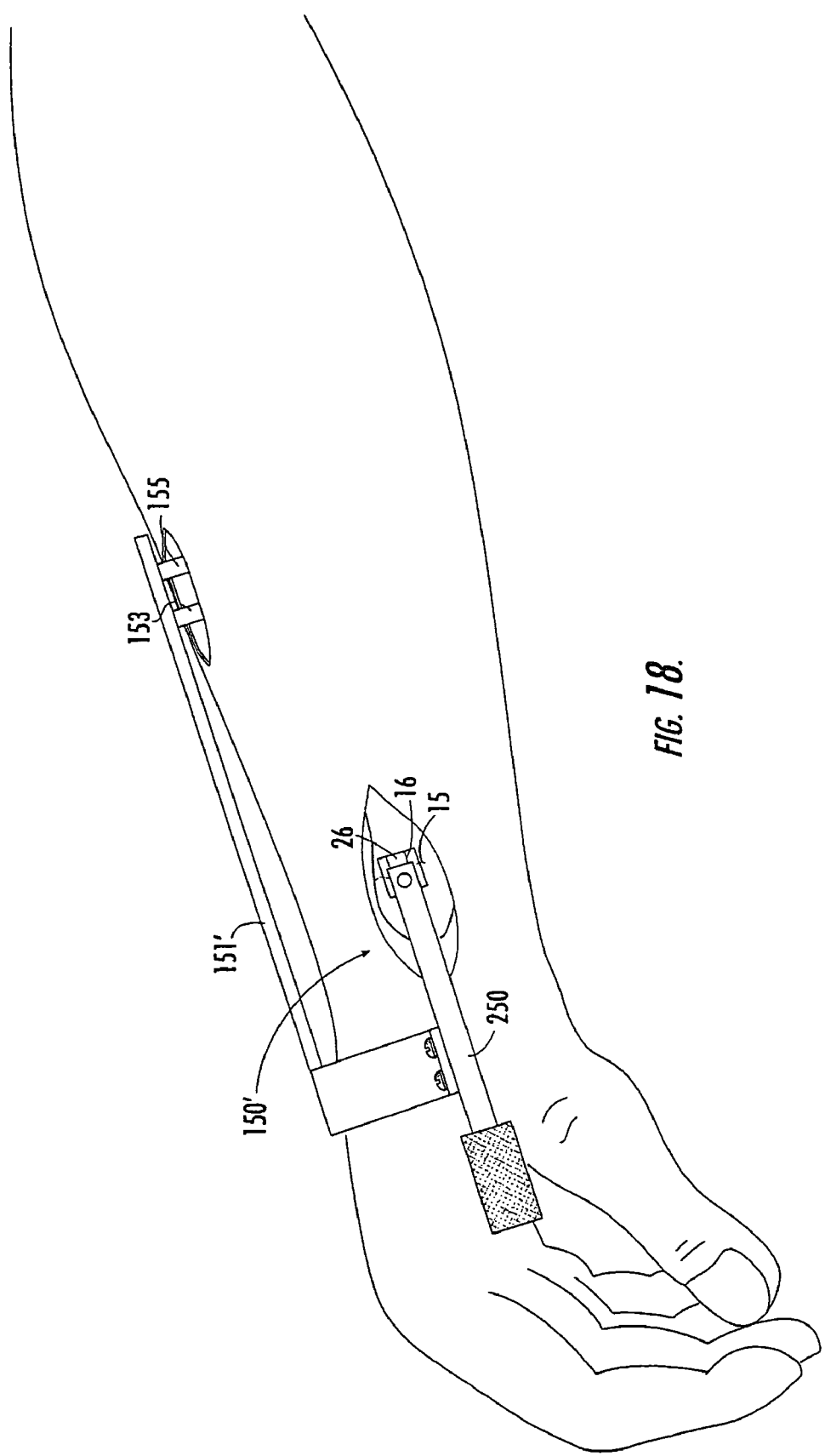
FIG. 18 is a side of the device shown in FIGS. 16 and 17 showing the device in position in the patient.
Figure 19:
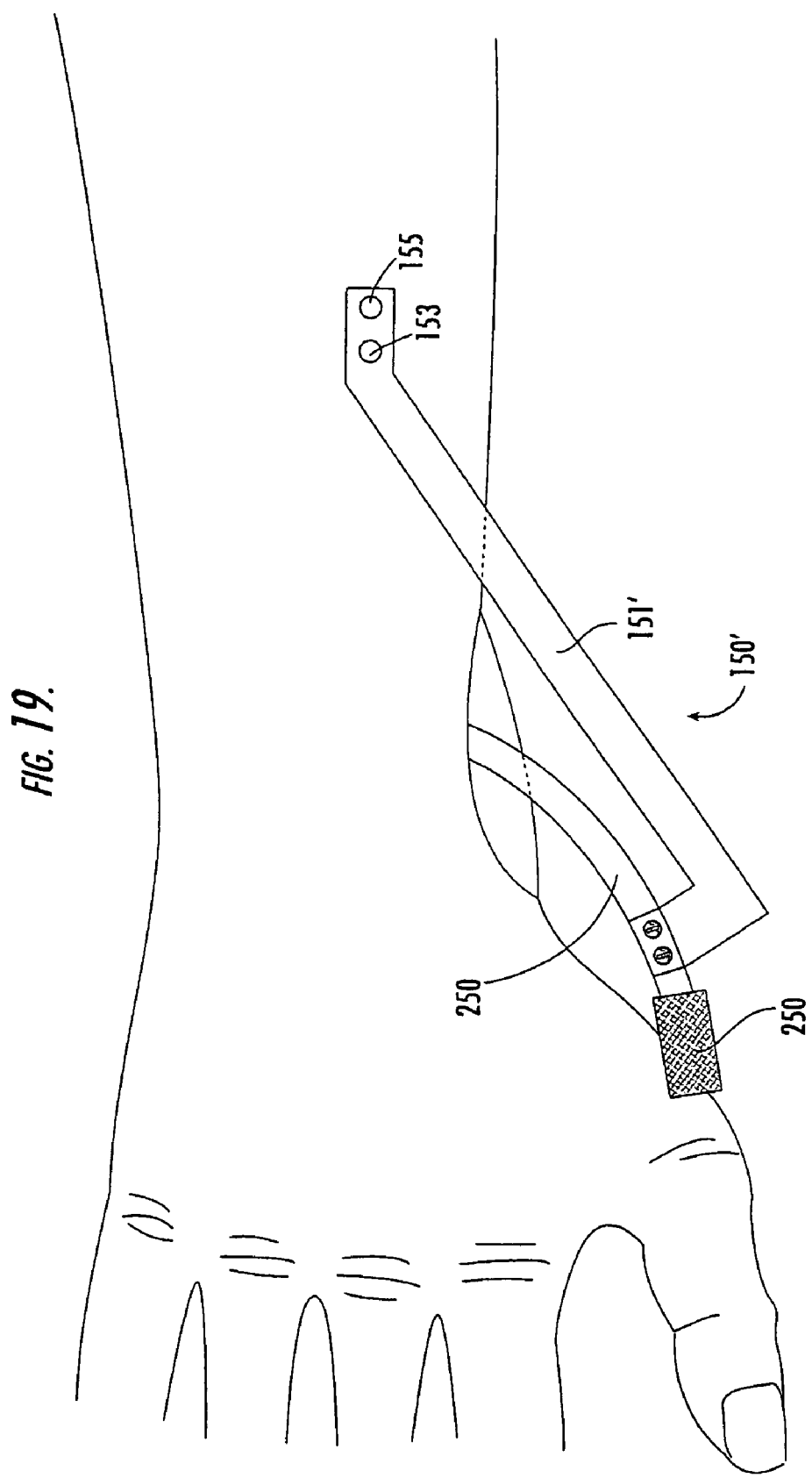
FIG. 19 is a top anterior-posterior view of the device shown in position in FIG. 18.
Figure 20:
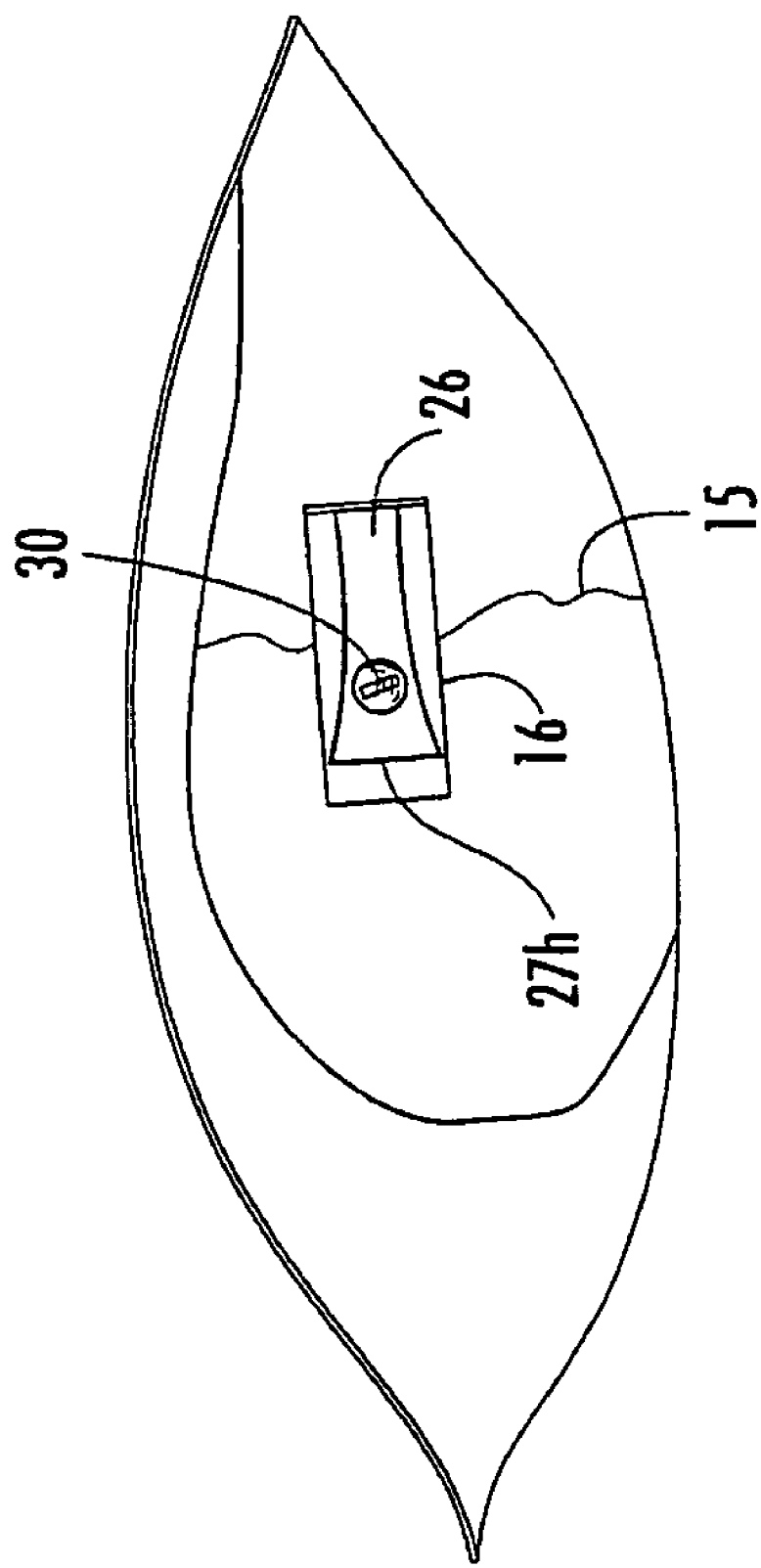
FIG. 20 is a schematic view of the fixation rod in position in the subject according to an embodiment of the present invention.

As shown in FIGS. 18 and 19, the rod driver 250 of the insertion guide 150' is used to direct the rod 26 into the intramedullary canal of the patient. The rod driver 250 allows a physician to direct the fixation rod 26 into the radius through the bone window 16. The position of the rod and the reduction of the fracture can be verified by a fluoroscopy unit. Once the rod 26 is in position, a small incision can be made so that the proximal attachment guides 153, 155 can be inserted therein. Traction may be appropriate to reduce the fracture at this time. The proximal attachment members 35a, 35b can then be inserted into the radius after the region has been drilled and/or tapped. Again, the proper positioning of the proximal attachment members 35a, 35b, can be verified by the fluoroscopy unit. The interlocking screw attachment guide 151' can then be removed from the patient and the rod driver 250. The rod driver 250 can be detached from the fixation rod 26 and the distal fixation member 30 can be inserted into the distal fragment and the fixation rod 26 as shown in FIG. 20.

Routine closure is performed on the incision sites and then, preferably, a long arm cast is applied to the patient. The typical healing process is about six weeks, during which time it is preferred that the treatment area be protected from undue stress and activity.

A rod according to the present invention can be formed from a number of suitable biocompatible materials including titanium, stainless steel, and cobalt chrome. Because the radius is not a weight bearing extremity, strength is not as important in this type of fixation rod as it might be in other fixation rod applications.

Surface coatings may also be used as appropriate. For example, as the device 25, 25', 25" chronically resides in the body, surface or other treatments may also be applied to, or integrated into, the rod 26 and/or the fixation members 30, 35 to achieve one or more of increased lubricity, low coefficient of friction (each for easier insertion) as well as increased tissue biocompatibility such as resistance to microbial growth and/or configured to reduce the incidence of inflammation or infection during healing. In one embodiment, the rod 26 comprises a material, at least on its exposed surfaces, which can inhibit the growth of undesirable microbial organisms. Preferably, the rod is coated with a biocompatible antimicrobial solution or coating which can inhibit the growth of bacteria, yeast, mold, and fungus. One suitable material may be the antimicrobial silver zeolite based product available from HealthShield Technologies LLC of Wakefield, Mass. Another alternative is a Photolink® Infection Resistance antimicrobial coating or a hemocompatible coating from SurModics, Inc. of Eden Prairie, Minn. The coating may also include other bioactive ingredients (with or without the antimicrobial coating), such as antibiotics, and the like. One product is identified as LubriLAST™ lubricious coatings from AST of Billerica, Mass.

In addition to, or alternatively, a rod according to the present invention can be configured with a biocompatible lubricant or low-friction material to help reduce any discomfort associated with the insertion of the device into the body. Coatings which may be appropriate include coatings which promote lubricity, and wettability. For example, a hydrophilic coating which is applied as a thin (on the order of about 0.5-50 microns thick) layer which is chemically bonded with UV light over the external surface of the rod 26. One such product is a hydrophilic polymer identified as Hydrolene® available from SurModics, Inc., of Eden Prairie, Minn. Other similar products are also available from the same source. Still further, the rod 26 can be configured not only to provide the lubricious coating but to also include bioactive ingredients configured to provide sustained release of antibiotics, antimicrobial, and anti-restenosis agents, identified as LubrilLast™ from AST as noted above.

Figure 11:
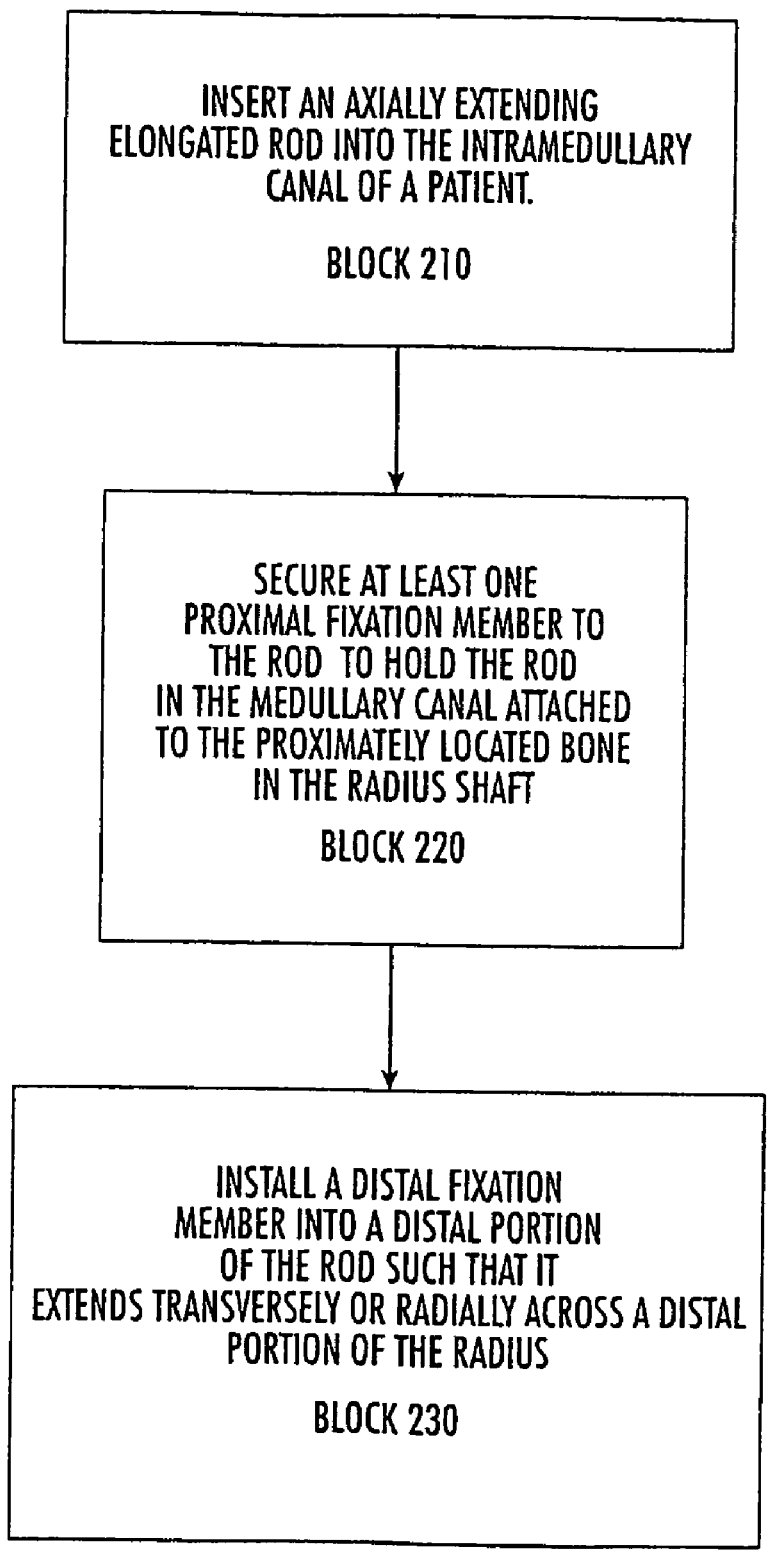
FIG. 11 is a block diagram of the steps of treating a distal radius fracture according to one embodiment of the present invention.

FIG. 11 illustrates the steps of a method for treating a fracture in the radius of a patient according to one embodiment of the present invention. An elongated axially extending rod is inserted into the intramedullary canal of the patient (Block 210). Proximal fixation members are then secured to the rod to hold the rod in the intramedullary canal attached to the proximately located bone in the radius shaft (Block 220). A distal fixation member is inserted into a distal portion of the rod such that it extends substantially medially or transversely across a distal portion of the radius (Block 230). A bone window may be formed into the radius to define an entry point for the rod (typically the window is formed into a small area of exposed bone which is present between the first and second compartments and covered only by periosteum) in the styloid region adjacent the two bone fragments.

The internal intramedullary radius fixation devices and associated treatment methods of the instant invention can provide improved or alternative treatment options over those conventionally available. The devices and methods of the instant invention may inhibit the collapse in the skeletal structure along the fracture fragment region and may be useful for the osteoporotic patient. The devices of the instant invention can also provide increased structural integrity and/or strength when in position in the distal radius fracture fragment.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, if used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed:

1. An internal fixation device for treating or repairing a distal radius fracture of a patient, the distal radius fracture having a fracture line forming distal and proximal fracture fragments, said device comprising:
an elongated fixation rod having distal and proximal portions, said distal portion including a head with a laterally extending distal aperture therein, wherein said elongated fixation rod has a curvilinear profile, from an anterior-posterior view, comprising a substantially linear proximal portion configured to axially extend within a medullary canal of the radius, wherein the substantially linear proximal portion defines an axial axis, the axial axis coincident with a centerline of the proximal portion of the rod, wherein the distal aperture is configured to receive a distal fixation member for attachment of said rod to the distal fracture fragment, wherein the rod is configured and sized to reside totally within the radius with the head entirely within a radial styloid region to support and buttress an articular surface of the distal radius and allow wrist mobility while stabilizing the distal radius fracture, and wherein from the anterior-posterior view, the rod curves radially away from the axial axis, distally from the linear portion, substantially following the contour of the distal radius, to position the head at the radial styloid region, and wherein the head has a surface that inclines in an ulnar direction toward the axial axis.

2. The device according to claim 1, wherein the distal portion of the rod has an increased cross-sectional area relative to the proximal portion.

3. The device according to claim 1, wherein the rod comprises a plurality of attachable segments.

4. The device according to claim 3, wherein the distal portion of the rod is matably attached to an intermediate portion of the rod.

5. The device according to claim 3, wherein the rod comprises a first distal segment providing said distal portion of the rod and a second proximal segment providing said proximal portion of the rod.

6. The device according to claim 1, wherein the distal portion of the rod is configured for removable attachment to an insertion guide adapted for positioning the rod in the patient.

7. The device according to claim 1, wherein the distal portion of the rod is configured for removable attachment to a drill guide adapted for guiding placement of a fixation member through the rod.

8. The device according to claim 1, wherein, post-operatively in position, said rod is configured and sized to be implanted within the patient such that the device is devoid of externally located members.

9. The device according to claim 1, wherein said rod has a size ranging from about 2.5-4.5 inches long and about 2.5-4.0 mm in width.

10. The device according to claim 1, wherein the head of the distal portion of the rod is configured with an increased perimeter relative to the proximal portion, and wherein said distal aperture angularly declines across a width of the rod so that, in position, a lowermost portion is located adjacent an ulna aspect of the distal radius.

11. The device according to claim 1, wherein the distal aperture is configured such that the distal fixation member, when in position, will angularly extend between about 10-90 degrees away from the axial axis.

12. The device according to claim 1, wherein the distal aperture is configured such that the distal fixation member, when in position, is oriented about 45 degrees with respect to the axial axis toward an ulnar aspect.

13. The device according to claim 1, further comprising a distal fixation member sized and configured to extend across substantially an entire width of the distal fracture fragment from a radial to an ulnar region, and sized and configured to reside internally in the distal radial bone to provide support to a central and an ulnar aspect of the distal radius fracture fragment.

14. The device according to claim 1, further comprising a distal fixation member sized and configured to extend across at least a major portion of a width but less than a full width of the distal fracture fragment in a metaphysis region of the distal radius to reside within the distal radius bone.

15. The device according to claim 14, wherein the distal fixation member is sized and configured to reside totally inside the radial styloid region of the distal radius and cooperate with the rod to affix distal radius fragments associated with the distal radius fracture.

16. The device according to claim 1, further comprising at least one proximal fixation member configured to secure the proximal portion of the fixation rod to the radius.

17. The device according to claim 1, further comprising means for anchoring the rod inside the medullary canal of the radius.

18. The device according to claim 1, wherein the proximal portion of the rod comprises a ribbed portion to inhibit rotation in the medullary canal.

19. The device according to claim 1, wherein the rod is sized and configured to enter a lateral entry bone window between first and second dorsal compartments in the distal radius for surgical placement in the radius.

20. An internal fixation device for treating or repairing a distal radius fracture of a patient, the distal radius fracture having a fracture line forming distal and proximal fracture fragments, said device comprising:
an elongated fixation rod having distal and proximal portions, the rod comprising a plurality of attachable segments, said distal portion including a head with a laterally extending distal aperture therein, wherein said elongated fixation rod has a curvilinear profile from an anterior-posterior view comprising a substantially linear proximal portion configured to axially extend within a medullary canal of the distal radius and a curved distal portion configured to extend from the proximal portion into a metaphysis region of the distal radius, wherein the substantially linear proximal portion defines an axial axis, the axial axis coincident with a centerline of the proximal portion of the rod, and wherein the distal aperture is configured to receive a distal fixation member for attachment of said rod to the distal fracture fragment, the distal portion of the rod being configured for removable attachment to a drill guide adapted for guiding placement of a fixation member through the rod, wherein the rod is configured and sized to reside totally within the radius with the head entirely within a radial styloid region to support and buttress an articular surface of the distal radius and allow wrist mobility while stabilizing the distal radius fracture, and wherein from the anterior-posterior view, the rod curves radially away from the axial axis, distally from the substantially linear portion, following the contour of the distal radius, to position the head at the radial styloid region, and wherein the head has an end surface that inclines in an ulnar direction toward the axial axis.

21. The device according to claim 20, wherein, post-operatively in position, said rod is configured and sized to be implanted within the patient such that the device is devoid of externally located members.

22. The device according to claim 20, further comprising a distal fixation member sized and configured to extend across at least a major portion of the width but less than a full width of the distal fracture fragment in a metaphysis region of the distal radius to reside within the distal radius bone.

23. The device according to claim 22, wherein the distal fixation member is sized and configured to reside totally inside the radial styloid region of the distal radius and cooperate with the rod to affix distal radius fragments associated with the distal radius fracture.

24. The device according to claim 20, further comprising an anchoring member adapted for affixing the proximal portion of the rod in a position relative to a shaft of the radius.

25. The device according to claim 20, wherein the proximal portion of the rod comprises a ribbed portion to inhibit rotation in the medullary canal.

26. The device according to claim 20, wherein the rod is sized and configured to enter a lateral entry bone window in the distal radius for surgical placement in the radius.

* * * * *

UNITED STATES PATENT AND TRADEMARK OFFICE
CERTIFICATE OF CORRECTION

PATENT NO.        : 8,100,910 B2
APPLICATION NO.   : 12/391459
DATED             : January 24, 2012
INVENTOR(S)       : Warburton Page 1 of 1

It is certified that error appears in the above-identified patent and that said Letters Patent is hereby corrected as shown below:

On the Title Page:
Item (*) Notice: insert -- This patent is subject to a terminal disclaimer. --

Item (56) References Cited, U.S. Patent Documents, Page 3, left column, Line 11:
correct "6,488,684  12/2002  Sterghos et al.
to read -- 6,488,684  12/2002  Bramlet et al.
Other Publications, Page 3, right column, Line 26, Orbay:
correct "Voter Fixation"
to read -- Volar Fixation --

Column 13, Claim 12, Line 12: delete "toward an ulnar aspect"

Signed and Sealed this
Eighth Day of May, 2012

David J. Kappos
*Director of the United States Patent and Trademark Office*